US010882823B2

(12) United States Patent
Miyazawa et al.

(10) Patent No.: US 10,882,823 B2
(45) Date of Patent: Jan. 5, 2021

(54) FLAVOR MODULATOR HAVING PYRIDINE DERIVATIVE OR SALT THEREOF AS ACTIVE INGREDIENT

(71) Applicant: T. HASEGAWA CO., LTD., Tokyo (JP)

(72) Inventors: Yamato Miyazawa, Kawasaki (JP); Yasutaka Ohkubo, Kawasaki (JP); Kenji Haraguchi, Kawasaki (JP); Michinaga Takahashi, Kawasaki (JP); Shogo Yoshida, Kawasaki (JP)

(73) Assignee: T. HASEGAWA CO., LTD., Tokyo (JP)

( * ) Notice: Subject to any disclaimer, the term of this patent is extended or adjusted under 35 U.S.C. 154(b) by 0 days.

(21) Appl. No.: 16/561,374

(22) Filed: Sep. 5, 2019

(65) Prior Publication Data

US 2019/0389801 A1 Dec. 26, 2019

Related U.S. Application Data

(60) Division of application No. 15/712,381, filed on Sep. 22, 2017, which is a continuation of application No. PCT/JP2016/061077, filed on Apr. 5, 2016.

(30) Foreign Application Priority Data

| Apr. 15, 2015 | (JP) | 2015-083656 |
| Sep. 15, 2015 | (JP) | 2015-181420 |
| Oct. 20, 2015 | (JP) | 2015-206337 |

(51) Int. Cl.

| *C07D 213/30* | (2006.01) |
| *A23L 27/00* | (2016.01) |
| *C07D 213/32* | (2006.01) |
| *A23L 23/10* | (2016.01) |
| *A23L 27/20* | (2016.01) |
| *A23C 9/13* | (2006.01) |
| *A23C 9/156* | (2006.01) |
| *A23G 9/32* | (2006.01) |
| *A23G 9/44* | (2006.01) |
| *A23G 9/52* | (2006.01) |
| *A23L 2/56* | (2006.01) |
| *A61K 8/02* | (2006.01) |
| *A61K 8/06* | (2006.01) |
| *A61K 8/49* | (2006.01) |
| *A61Q 11/00* | (2006.01) |
| *A61Q 13/00* | (2006.01) |
| *A61Q 5/02* | (2006.01) |

(52) U.S. Cl.
CPC .......... *C07D 213/30* (2013.01); *A23C 9/1307* (2013.01); *A23C 9/156* (2013.01); *A23G 9/32* (2013.01); *A23G 9/44* (2013.01); *A23G 9/52* (2013.01); *A23L 2/56* (2013.01); *A23L 23/10* (2016.08); *A23L 27/00* (2016.08); *A23L 27/20* (2016.08); *A23L 27/2054* (2016.08); *A23L 27/80* (2016.08); *A23L 27/88* (2016.08); *A61K 8/022* (2013.01); *A61K 8/06* (2013.01); *A61K 8/4926* (2013.01); *A61K 8/4933* (2013.01); *A61Q 11/00* (2013.01); *A61Q 13/00* (2013.01); *C07D 213/32* (2013.01); *A23G 2200/00* (2013.01); *A23V 2002/00* (2013.01); *A61Q 5/02* (2013.01)

(58) Field of Classification Search
CPC ...... C07D 213/30; C07D 213/32; A23G 9/32; A23G 9/44; A23G 9/52; A23G 2200/00; A23C 9/1307; A23C 9/156; A23L 27/80; A23L 2/56; A23L 27/2054; A23L 27/00; A23L 27/20; A23L 27/88; A23L 23/10; A61Q 13/00; A61Q 11/00; A61Q 5/02; A61K 8/4933; A61K 8/022; A61K 8/06; A61K 8/4926; A23V 2002/00
See application file for complete search history.

(56) References Cited

U.S. PATENT DOCUMENTS

| 4,036,844 A | 7/1977 | Thorne et al. |
| 10,178,875 B2 | 1/2019 | Bom |

FOREIGN PATENT DOCUMENTS

| CN | 101238203 A | | 8/2008 |
| DE | 842995 | | 7/1952 |
| GB | 1437781 | * | 6/1976 |
| JP | 49-100091 | | 9/1974 |
| JP | 2011-516059 A | | 5/2011 |
| JP | 2012-070636 A | | 4/2012 |
| JP | 2012-532848 A | | 12/2012 |

(Continued)

OTHER PUBLICATIONS

International Preliminary Report on Patentability for corresponding PCT International Application No. PCT/JP2016/061077, dated Jul. 5, 2016, with English translation.
International Search Report for corresponding PCT International Application No. PCT/JP2016/061077.
CAS 1624310-86-6 Abstract dated Jun. 23, 2016.
CAS 1623685-28-8 Abstract dated Jun. 23, 2016.
Izvestiya Akademii Nauk SSSR, Seriya Khimicheskaya, (7);1628-34(14) (1986).
Cadu et al., Iridium-Catalyzed Asymmetric Hydrogenation of Substituted Pyridines, Asian Journal of Organic Chemistry, 2(12):1061-1065 (2013).

(Continued)

*Primary Examiner* — Cephia D Toomer
(74) *Attorney, Agent, or Firm* — Browdy and Neimark, PLLC

(57) ABSTRACT

2-(phenylalkyloxyalkyl)pyridine derivative or a 2-(phenylalkylthioalkyl)pyridine derivative imparts, when added to food and drink or cosmetics as an active ingredient, a flavor of natural impression thereto; and in particular, when added to food and drink, the compound imparts an umami imparting or enhancing, a saltiness enhancing a sweetness enhancing, and in particular, when added to a milk or dairy product, a food or drink product containing a milk or dairy product, or a dairy replacement product, the compound provides a milk richness enhancing.

3 Claims, No Drawings

(56) References Cited

FOREIGN PATENT DOCUMENTS

| JP | 5500664 | B1 | 5/2014 |
| JP | 2014-531448 | A | 11/2014 |
| JP | 5805902 | B1 | 11/2015 |
| WO | 2015/000900 | A2 | 1/2015 |

OTHER PUBLICATIONS

Legault et al., Catalytic Asymmetric Hydrogenation of N-Iminopyridinium Ylides: Expedient Approach to Enantioenriched Substituted Piperidine Derivatives, Journal of the American Chemical Society,127(25), 8966-8967 (2005).

Fleury-Brégeot, Suzuki-Miyaura Cross-Coupling of Potassium Alkoxyethyltrifluoroborates: Access to Aryl/Heteroarylethyloxy Motifs, J. Org. Chem., 77:10399-10408 (2012).

Japan Patent Office, Glossary of Well-Known Conventional Techniques (flavors), Part II, Food Flavors, pp. 8-87, published Jan. 14, 2000).

Cohen et al., GRAS 28 Flavoring Substances, Food/Technology, pp. 63-78 (Jul. 2018).

Maga, "Pyridines in Foods", Journal of Agricultural and Food Chemistry, pp. 895-898, vol. 29, No. 5 (Sep./Oct. 1981).

Office Action dated Sep. 17, 2019 for U.S. Appl. No. 15/712,381.

Office Acmion dated Apr. 27, 2020, issued in corresponding Chinese patent application No. 201680018985.8 with its English Machine translation.

Office Action dated Feb. 14, 2020, issued in parent U.S. Appl. No. 15/712,381.

Office Acmion dated Oct. 26, 2020, issued in corresponding Chinese patent application No. 201680018985.8 with its English Machine translation.

* cited by examiner

FLAVOR MODULATOR HAVING PYRIDINE DERIVATIVE OR SALT THEREOF AS ACTIVE INGREDIENT

This application is a Continuation of PCT International Application No. PCT/JP2016/061077, filed Apr. 5, 2016, which claims priority under 35 U.S.C. Section 119(a) to Japanese Patent Application No. 2015-083656 filed on Apr. 15, 2015, Japanese Patent Application No. 2015-181420 filed on Sep. 15, 2015 and Japanese Patent Application No. 2015-206337 filed on Oct. 20, 2015. Each of the above applications is hereby expressly incorporated by reference, in its entirety, into the present application.

BACKGROUND OF THE INVENTION

Technical Field of the Invention

The present invention relates to a flavor modulator having a pyridine derivative or a salt thereof as an active ingredient. More precisely, the present invention relates to a flavor composition for foods that uses the flavor modulator, to a food or drink product that uses the flavor modulator or the flavor composition for foods, to a flavor composition for cosmetics, and to a cosmetic product using the flavor modulator or the flavor composition for cosmetics. Further, the present invention relates to a flavor imparting or enhancing agent for food and drink or for cosmetics that uses a pyridine derivative or a salt thereof, to an umami imparting or enhancing method for food and drink, to a sweetness enhancing method for food and drink, to a saltiness enhancing method for food and drink, to a richness enhancing method for milk, and to an emulsified composition. Further, the present invention relates to a powder composition using the emulsified composition. Further, the present invention relates to a novel pyridine derivative or a salt thereof.

Background Art

Recently, in flavors for food and drink and for cosmetics, there is an increasing need for flavors having a new type of unprecedented odor/taste with diversification of consumers' preferences, and development of unique flavor materials having mild and fresh flavor quality and excellent in sustainability is desired. Given the situation, studies for preparing flavor compositions that may feel as natural as possible are being made by combining flavor materials adequately or with changing the compounding ratio thereof, but could not be said to be sufficient. Consequently, searches for various organic compounds as new flavor materials are being made.

Flavor compounds are compounds that stimulate a sense of smell, and it is said that tens of thousands of kinds of such compounds are known. On the other hand, it is considered that the flavor of food is a sense of olfactory stimulus and taste stimulus integrated in the brain. Specifically, olfactory stimulus is combined with a compound that stimulates a sense of taste (salt, sugar, sodium glutamate, etc.) to constitute an entire flavor of food. Recently, among aroma compounds, those that stimulate both a sense of taste and a sense of smell are searched for actively, and are used for improving a total flavor of food and drink.

As a compound that stimulates both a sense of smell and a sense of taste, for example, 4-hydroxy-2(5)-ethyl-5(2)-methyl-3(2H)-furanone has been found to have an effect of enhancing saltiness when added to soy sauce (Patent Document 1). In addition, 1,3,5-undecatriene has been found to have an additional effect of enhancing a carbonic taste similar to salt stimulation when added to carbonated drink (Patent Document 2). In general, many flavor compounds produce a bitter taste relative to a sense of taste. Above all, menthol that is a typical flavor compound is known to have a cooling taste as an olfactory stimulus effect, but apart from the olfactory stimulus effect, the compound is also known to produce a cooling feel on the skin or on the mouth as a pain sensation effect, thereby having a bitter taste as a taste stimulus effect.

Regarding umami (delicious taste) as a basic taste, compounds that stimulate both a sense of smell and a sense of taste have been found among aroma compounds, and by applying these compounds as food aromas, the functionality of food and drink is expanded to provide a new taste that consumers desire. For example, 2-alkylpyridines are disclosed to have umami (Patent Document 3). In addition, aromatic ketone compounds having a pyridine ring-containing substituent (Patent Document 4) and aromatic amide compounds (PATENT DOCUMENT 5) are also disclosed as umami substances.

In addition, 2-(2-benzyloxyethyl)pyridine that is a kind of 2-(phenylalkyloxyalkyl)pyridines is reported as a product of a nitrile compound and acetylene in pyridine ring synthesis reaction studies (Non-Patent Document 1) and in coupling reaction studies utilizing an organic metal (Non-Patent Document 2), and use thereof as an umami enhancer is disclosed (PATENT DOCUMENT 6).

CITATION LIST

Patent Literature

PATENT DOCUMENT 1: JP 2012-70636A
PATENT DOCUMENT 2: JP 5500664B
PATENT DOCUMENT 3: JP 2011-516059T
PATENT DOCUMENT 4: JP 2012-532848T
PATENT DOCUMENT 5: JP 2014-531448T
PATENT DOCUMENT 6: WO2015/000900

Non-Patent Literature

NON-PATENT DOCUMENT 1: Izvestiya Akademii Nauk SSSR, Seriya Khimicheskaya (1986), (7), 1628-34
NON-PATENT DOCUMENT 2: Journal of Organic Chemistry (2012), 77(22), 10399-10408

SUMMARY OF INVENTION

An object of the present invention is to provide a flavor compound which, when added to food and drink or to cosmetics, imparts or enhances a favorable flavor, or when added to food and drink, imparts not only a flavor but also umami as a favorable taste and further enhances umami, sweetness, saltiness and richness of milk, and to provide a flavor composition containing the compound as an active ingredient, as well as a food or drink product and a cosmetic product containing the compound as an active ingredient.

The present inventors have assiduously studied a large number of organic compounds and, as a result, have found that a compound represented by the following formula (1), a 2-(phenylalkyloxyalkyl)pyridine derivative or a 2-(phenylalkylthioalkyl)pyridine derivative has a herbal, earthy, almond, nutty or rummy flavor, and regarding the taste thereof, the compound provides, when added to food and drink in a high concentration, a somewhat bitter, vegetable-like or spicy taste, but when added thereto in a low concentration, exhibits an effect of enhancing umami, sweetness, saltiness and milk richness of food and drink, and that the effect thereof of enhancing umami and others is significantly higher than that of 2-(2-benzyloxyethyl)pyridine, and have completed the present invention.

In addition, the present inventors have further assiduously studied a large number of organic compounds and, as a result, have found that a compound represented by the following formula (11) where the number of carbon atoms in the side chain on the pyridine side of the ether bond of 2-(2-benzyloxyethyl)pyridine is increased by one, 2-(3-benzyloxypropyl)pyridine has a herbal, green or nutty flavor of natural impression, and regarding the taste thereof, the compound provides, when added to food and drink in a high concentration, a somewhat bitter, vegetable-like or spicy taste, but when added thereto in a low concentration, exhibits an effect of enhancing umami, sweetness, saltiness and milk richness of food and drink, and that the effect thereof of enhancing umami and others is higher by about 10 times than that of 2-(2-benzyloxyethyl)pyridine.

2-(3-Benzyloxypropyl)pyridine represented by the formula (11) is a compound reported in organic chemical reaction studies (Asian Journal of Organic Chemistry (2013), 2(12), 1061-1065; Journal of the American Chemical Society (2005), 127(25), 8966-8967; German Registered Patent 842995), but there is no report relating to the physiological effect thereof, especially the flavor and the taste thereof, and use of the compound as a flavor material for food and drink or for cosmetics, as well as use thereof as an umami or sweetness enhancing agent for food and drink is not known.

The present inventors have further assiduously studied 2-(3-benzyloxypropyl)pyridine and, as a result, have found that an emulsified composition containing the compound, or a powdery composition thereof prepared by drying the emulsified composition can be readily incorporated in various food and drink products and in cosmetics and, in addition, can be used as a material having a high-level flavor modulating effect.

With that, the present invention provides the following:

[1] A flavor modulator containing, as an active ingredient, a compound represented by the following formula (1) or a salt thereof.

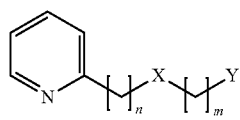
(1)

In the above formula (1), n=2, 3, 4 or 5, m=1 or 2, X represents O or S, Y represents the following formula (2) or (3).

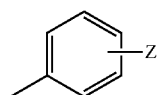
(2)

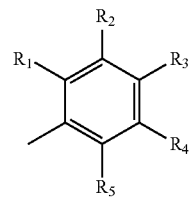
(3)

In the above formula (2), Z represents a hydrogen atom, an alkyl group having 1 to 4 carbon atoms, or a group OR (where R represents a hydrogen atom, or an alkyl group having 1 to 4 carbon atoms) (provided that a case where n=2 and m=1 is excluded). In the above formula (3), $R_1$ to $R_5$ each represent a hydrogen atom or a methyl group, and at least two of $R_1$ to $R_5$ are methyl groups.

[2] The flavor modulator according to [1], wherein the compound represented by the formula (1) is 2-(3-benzyloxypropyl)pyridine represented by the following formula (11) as an active ingredient.

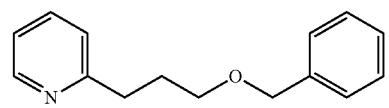
Formula (11)

[3] The flavor modulator according to [1] or [2], wherein the flavor modulation is flavor impartment or enhancement.
[4] The flavor modulator according to [1] or [2], wherein the flavor modulation is umami impartment.
[5] The flavor modulator according to [1] or [2], wherein the flavor modulation is umami enhancement.
[6] The flavor modulator according to [1] or [2], wherein the flavor modulation is sweetness enhancement.
[7] The flavor modulator according to [1] or [2], wherein the flavor modulation is saltiness enhancement.
[8] The flavor modulator according to [1] or [2], wherein the flavor modulation is milk richness enhancement for a milk or dairy product, a food or drink product containing a milk or dairy product, or a dairy replacement product.
[9] A flavor composition for food and drink, containing the flavor modulator according to any one of [1] to [8] as an active ingredient.
[10] A food or drink product containing the flavor modulator according to any one of [1] to [8] or the flavor composition for food and drink according to [9].
[11] The flavor composition for cosmetics containing the flavor modulator according to any one of [1] to [3] as an active ingredient.
[12] A cosmetic product containing the flavor modulator according to any one of [1] to [3] or the flavor composition for cosmetics according to [11].
[13] A flavor imparting or enhancing method for food and drink or cosmetics, wherein a compound represented by the formula (1) or a salt thereof in [1] is contained in a food or drink product or in a cosmetic product.
[14] An umami imparting or enhancing method for food and drink, wherein a compound represented by the formula (1) or a salt thereof in [1] is contained in a food or drink product.
[15] A sweetness enhancing method for food and drink, wherein a compound represented by the formula (1) or a salt thereof in [1] is contained in a food or drink product.

[16] A saltiness enhancing method for food and drink, wherein a compound represented by the formula (1) or a salt thereof in [1] is contained in a food or drink product.
[17] A milk richness enhancing method for a milk or dairy product, a food or drink product containing a milk or dairy product, or a dairy replacement product, wherein a compound represented by the formula (1) or a salt thereof in [1] is contained in a milk or dairy product, a food or drink product containing a milk or dairy product, or a dairy replacement product.
[18] An emulsified composition containing the following (A) to (D):
(A) A compound represented by the formula (1) or a salt thereof in [1].
(B) Water.
(C) One or more selected from sugars, monoalcohols or polyalcohols.
(D) An emulsifier.
[19] A powder composition produced by drying the emulsified composition in [18].
[20] A compound represented by the following formula (4) or a salt thereof:

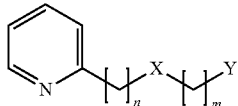

(4)

In the formula (4), n=2, 3, 4 or 5, m=1 or 2, X represents O or S, and Y represents the following formula (5) or (6):

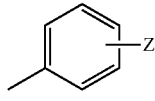

(5)

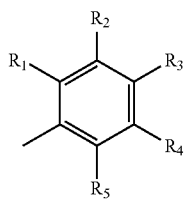

(6)

In the above formula (5), Z represents a hydrogen atom, an alkyl group having 1 to 4 carbon atoms or a group OR (where R represents a hydrogen atom or an alkyl group having 1 to 4 carbon atoms) (provided that a case where n=2 and m=1, or a case where n=3 or 4 and m=1, X is O and Z is H is excluded). In the above formula (6), $R_1$ to $R_5$ each represent a hydrogen atom or a methyl group, and at least two of $R_1$ to $R_5$ are methyl groups.

A 2-(phenylalkyloxyalkyl)pyridine derivative or a 2-(phenylalkylthioalkyl)pyridine derivative, a compound represented by the above formula (1) or a salt thereof of the compound of the present invention imparts, when added to food and drink or cosmetics, a herbal, green, nutty, earthy, almond or rummy flavor thereto, and in particular, when added to food and drink, imparts thereto a flavor of natural impression, and additionally provides an umami imparting or enhancing effect and a sweetness and saltiness enhancing effect, and in particular, when added to a milk or dairy product, a food or drink product containing a milk or dairy product, or a dairy replacement product, the compound provides a milk richness enhancing effect.

2-(3-Benzyloxypropyl)pyridine, a compound of a preferred embodiment of the present invention provides, when added to food and drink or cosmetics, a somewhat herbal, green or natty flavor of natural impression, and in particular, when added to food and drink, the compound imparts a flavor of natural impression thereto and also provides an umami imparting or enhancing effect and a sweetness and saltiness enhancing effect, and in particular, when added to a milk or dairy product, a food or drink product containing a milk or dairy product, or a dairy replacement product, the compound provides a milk richness enhancing effect.

DESCRIPTION OF EMBODIMENTS

The present invention is described in more detail hereinunder.

A compound represented by the following formula (1) of the present invention, 2-(phenylalkyloxyalkyl)pyridine derivative or a 2-(phenylalkylthioalkyl)pyridine derivative provides, as described above, when added to food and drink in a high concentration, a somewhat bitter, vegetable-like or spicy taste, but when added thereto in a low concentration, the compound provides an effect of enhancing umami, sweetness, saltiness and milk richness of food and drink.

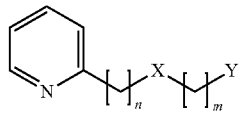

(1)

In the above formula (1), n=2, 3, 4 or 5, m=1 or 2, X represents O or S, Y represents the following formula (2) or (3).

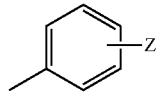

(2)

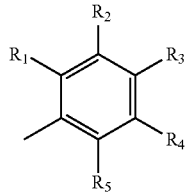

(3)

In the above formula (2), Z represents a hydrogen atom, an alkyl group having 1 to 4 carbon atoms, or a group OR (where R represents a hydrogen atom, or an alkyl group having 1 to 4 carbon atoms) (provided that a case where n=2 and m=1 is excluded). In the above formula (3), $R_1$ to $R_5$ each represent a hydrogen atom or a methyl group, and at least two of $R_1$ to $R_5$ are methyl groups.

Regarding the compound represented by the above formula (1) of the present invention, use of a salt of the compound provides the same effect as the above-mentioned effect of the compound in adding to food and drink or cosmetics. In particular, for the case of adding to food and drink, an edible salt of the compound represented by the above formula (1) is preferred, for example, including hydrochlorides, phosphates, citrates, lactates, malates, gluconates, maleates, fumarates, succinates, tartrates, etc.

In particular, when Z is positioned at the para-position as shown in the following formula (7), the compound provides a more favorable umami, sweetness, saltiness and milk richness enhancing effect for food and drink.

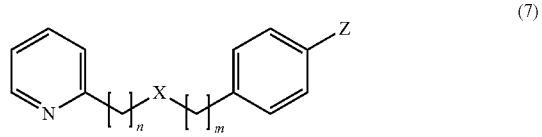

(7)

In the above formula (7), n=2, 3, 4 or 5, m=1 or 2, X represents O or S, Y represents a hydrogen atom, an alkyl group having 1 to 4 carbon atoms, or a group OR (where R represents a hydrogen atom or an alkyl group having 1 to 4 carbon atoms) (provided that a case where n=2 and m=1 is excluded).

Specific examples of the compound include 2-(3-benzyloxypropyl)pyridine, 2-(4-benzyloxybutyl)pyridine, 2-(4-benzyloxybutyl)pyridine hydrochloride, 2-(5-benzyloxypentyl)pyridine, 2-(2-phenylethoxyethyl)pyridine, 2-83-phenylethoxypropyl)pyridine, 2-[3-(p-methoxybenzyloxy) propyl]pyridine, 2-[3-(p-ethoxybenzyloxy)propyl]pyridine, 2-[3-(p-isopropyloxybenzyloxy)propyl]pyridine, 2-(2-phenylethylthioethyl)pyridine, 2-(2-phenylethylthioethyl)pyridine hydrochloride, 2-(3-phenylethylthiopropyl)pyridine, 2-[3-(p-methylbenzyloxy)propyl]pyridine, 2-[3-(p-ethylbenzyloxy)propyl]pyridine, 2-[3-(2,5-dimethylbenzyloxy) propyl]pyridine, 2-[3-(2,6-dimethylbenzyloxy)propyl]pyridine. These compounds have an effect of enhancing umami, sweetness, saltiness and milk richness of food and drink.

2-(3-Benzyloxyproyl)pyridine, a compound represented by the formula (11) is, as described above, a known compound as a substance, and can be synthesized according to the known method described in the above-mentioned literature, but as a simpler method, the compound can be readily produced utilizing synthesis reaction shown by the following formula.

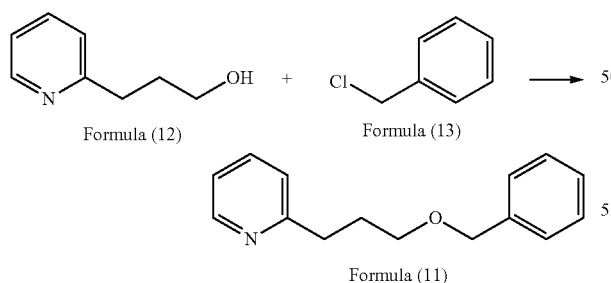

According to the above reaction formula, the compound can be efficiently produced through etherification of 2-pyridinepropanol represented by the formula (12) and benzyl chloride represented by the formula (13) in a suitable solvent in the presence of a base such as sodium hydroxide, sodium hydride, etc. The resultant compound of the formula (11) can be highly purified according to a method of distillation under reduced pressure or the like.

For example, 2-(4-benzyloxybutyl)pyridine is a known compound, and can be prepared by utilizing synthesis reaction according to the following scheme.

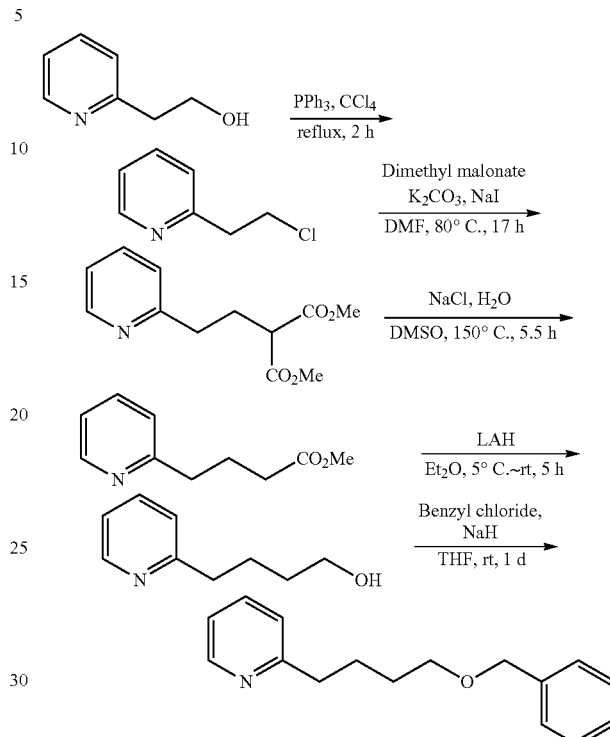

Specifically, a starting material of 2-pyridine-ethanol is chlorinated to give 2-(2-chloroethyl)pyridine, then dimethyl 2-(2-pyridyl)ethylmalonate is produced through malonate synthesis, thereafter methyl 4-(2-pyridyl)butyrate is produced through hydrolysis and decarboxylation, and this is reduced with lithium aluminium hydride and then benzyl chloride is added thereto to give 2-(4-benzyloxybutyl)pyridine.

In addition, for example, 2-(2-phenylethoxyethyl)pyridine is a novel compound, and can be produced by utilizing synthesis reaction according to the following scheme.

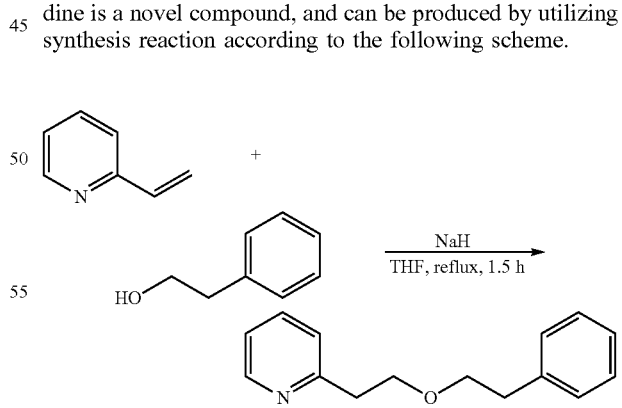

Specifically, 2-vinylpyridine and 2-phenylethyl alcohol are reacted in the presence of sodium hydride to prepare 2-(2-phenylethoxyethyl)pyridine.

Further, for example, 2-[3-(p-methoxybenzyloxy)propyl] pyridine is a novel compound, and can be prepared utilizing synthesis reaction according to the following scheme.

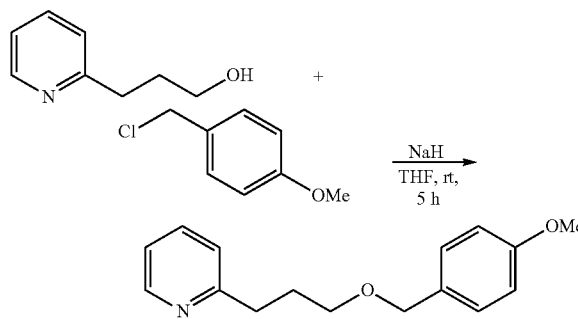

Specifically, 2-pyridinepropanol and p-methoxybenzyl chloride are reacted in the presence of sodium hydride to prepare 2-[3-(p-methoxybenzyloxy)propyl]pyridine.

These resultant compounds can be highly purified according to a method of distillation under reduced pressure, column chromatography or the like.

The present invention provides a flavor modulator, an umami imparting agent, an umami or sweetness enhancer, as well as a flavor composition containing a compound represented by the above formula (1) or a salt thereof as an active ingredient, and a food or drink product and a cosmetic product containing these.

A preferred embodiment of the present invention includes a flavor modulator, an umami imparting agent, an umami enhancer, a sweetness enhancer, a saltiness enhancer and a milk richness enhancer, as well as a flavor composition containing 2-(3-benzyloxypropyl)pyridine as an active ingredient, as well as a food or drink product and a cosmetic product containing them.

A compound represented by the above formula (1) or a salt thereof, which is an active ingredient in the present invention, has a herbal, earthy, almond, nutty, or rummy flavor, and in the case where the compound represented by the formula (1) or a salt thereof is used for flavor impartation, it may be added to food and drink or to cosmetics in an amount generally within a range of 0.1 ppb to 200 ppm based on the mass of the compound of the formula (1), preferably 1 ppb to 20 ppm, more preferably 10 ppb to 2 ppm. By adding thereto within the concentration range, food and drink or cosmetics can be given a flavor of natural impression.

2-(3-Benzyloxypropyl)pyridine, an active ingredient in a preferred embodiment of the present invention, has a somewhat herbal or green nutty flavor of natural impression, and in the case where 2-(3-benzyloxypropyl)pyridine is used for flavor impartation, the compound may be added to food and drink or to cosmetics in an amount generally within a range of 0.1 ppb to 200 ppm based on the mass of 2-(3-benzyloxypropyl)pyridine, preferably 1 ppb to 20 ppm, more preferably 10 ppb to 2 ppm. By adding the compound thereto within the concentration range, food and drink or cosmetics can be given a herbal, green or nutty flavor of natural impression.

When the compound represented by the above formula (1) or a salt thereof is diluted alone in water, the resultant aqueous solution provides umami, and the concentration thereof to provide a taste of umami is, based on mass, within a range of 0.01 ppm to 200 pm, but is, for exemplification, preferably within a range of 0.1 ppm to 20 ppm.

However, when combined with an umami ingredient such as salt, sodium glutamate or the like, or when combined with a volatile umami enhancer such as 2,4,7-tridecatrienal, 4,7-tridecadienal, trimethylamine, 2-methylfuran-3-thiol or the like, the compound or a salt thereof exhibits a synergistic umami and saltiness enhancing effect, and the concentration of the compound represented by the formula (1) or a salt thereof to exhibit the synergistic effect is, based on the mass of food and drink, within a range of 0.1 ppb to 40 ppm, preferably 1 ppb to 10 ppm, more preferably 5 ppb to 2 ppm.

When combined with a sweet substance such as sucrose or the like, the compound represented by the formula (1) or a salt thereof exhibits a sweetness enhancing effect, and the concentration thereof to exhibit the synergistic effect is, based on the mass of food and drink, within a range of 0.1 ppb to 40 ppm, preferably 1 ppb to 10 ppm, more preferably 5 ppb to 2 ppm.

In particular, when added to a milk or dairy product, a food or drink product containing a milk or dairy product, or a dairy replacement product, the compound represented by the formula (1) or a salt thereof of the present invention well exhibits the umami enhancing, saltiness enhancing and sweetness enhancing effect thereof, and gives a feeling of milk richness enhancement. The concentration of the compound or a salt thereof to exhibit the effect is, based on the mass of a milk or dairy product, a food or drink product containing a milk or dairy product, or a dairy replacement product, within a range of 0.1 ppb to 40 ppm, preferably 1 ppb to 10 ppm, more preferably 5 ppb to 2 ppm.

Examples of umami materials whose umami can be enhanced owing to the synergistic effect with the compound represented by the formula (1) or a salt thereof of the present invention include inorganic salts such as edible salt, potassium chloride or the like as salty substances; and as umami substances, amino acids such as sodium glutamate, aspartic acid, serine, theanine, arginine, etc., peptides such asdipeptide, oligopeptide, etc., nucleic acids such as inosinic acid, guanylic acid, etc., organic acids such as succinic acid, etc., and arbitrary mixtures thereof, etc.

Examples of sweet materials whose sweetness can be enhanced owing to the synergistic effect with the compound represented by the formula (1) or a salt thereof of the present invention include sugars such as sucrose, glucose, fructose, maltose, lactose, galactose, maltitose, trehalose, etc.; high intensity sweeteners such as acesulfame K, sucralose, aspartame, neotame, disodium glycyrrhizinate, thaumatin, saccharin and a salt thereof, momordica grosvenori extract, licorice extract, Rebaudioside A, stevia extract, enzyme-processed stevia extract, neohesperidin dihydrochalcone, etc.; sugar alcohols such as xylitol, erythritol, sorbitol, maltitol, palatinit, reduced sugar syrup, etc.; and arbitrary mixtures thereof, etc.

Examples of milks, dairy products, food or drink products containing a milk or dairy product, or dairy replacement products whose richness is especially enhanced by the compound represented by the formula (1) or a salt thereof of the present invention are mentioned below. Examples of milks include raw milk, cow milk, certified milk, partially skimmed milk, processed milk and others as specified in "Ordinance regarding standard of element, etc. of milk and dairy products" (Ordinance of the Health and Welfare Ministry No. 52, Dec. 27, 1951); examples of dairy products include cream, butter, butter oil, fermented milk such as yoghurt or the like, lactobacillus beverage, milk beverage, cheese, ice creams, concentrated milk, skimmed concentrated milk, condensed milk, whole milk powder, skimmed milk powder, sweetened milk powder, concentrated whey, whey powder and others as specified in the above-mentioned Ordinance; examples of food or drink products containing a milk or dairy product include coffee drinks, tea drinks, fruit juice drinks, carbonated drinks, frozen desserts, Japanese or western-style confectionery products, baked goods, soups, curries, stews, various ready-to-serve food and drink products, various snack food products, seasonings such as dressings and the like added with cow milk, cream, butter, cheese, condensed milk, powdered milk and the like; examples of dairy replacement products include butter replacement products such as margarine, fast spread and the like to be produced by emulsifying oils and fats, cream replacement products such as coffee whitener or the like to be added to coffee, tea or the like, etc.

In the case where the compound represented by the formula (1) or a salt thereof is added to a food or drink product or to a cosmetic product, the compound represented by the formula (1) or a salt thereof itself or one prepared by diluting it may be added to a food or drink product or to a cosmetic product, but apart from this, a flavor composition containing the compound represented by the formula (1) or a salt thereof as an active ingredient may be prepared, and the flavor composition may be added to a food or drink product or to a cosmetic product to thereby make the food or drink product or the cosmetic product have a flavor. In addition, by imparting a flavor to a food or drink product, and by adding the compound represented by the formula (1) or a salt thereof to a flavor composition as an active ingredient therein followed by adding the flavor composition to the food or drink product, umami of the food or drink product can be enhanced.

The flavor composition of the present invention may contain the compound represented by the formula (1) or a salt thereof generally in a concentration of 0.1 ppm to 2% based on the mass of the flavor composition, preferably 1 ppm to 0.5%, more preferably 10 ppm to 0.1%.

Further, in the case where the flavor composition is used for imparting a flavor to food and drink or cosmetics, the composition is added thereto in an amount of approximately 0.01% to 1% so that the addition concentration of the compound represented by the formula (1) or a salt thereof in the food or drink product or in the cosmetic product could be within a range of 0.1 ppb to 200 ppm by mass, preferably 1 ppb to 20 ppm, more preferably 10 ppb to 2 ppm. As a result, the compound represented by the formula (1) or a salt thereof can act on the food or drink product or on the cosmetic product as an active ingredient, thereby imparting a herbal, green, earthy, almond, nutty or rummy flavor of natural impression to the food or drink product or to the cosmetic product. Preferably, the compound represented by the formula (1) acts on a food or drink product or on a cosmetic product as an active ingredient to thereby impart a herbal, earthy, almond, nutty or rummy flavor to the food or drink product or to the cosmetic product.

In the case where the flavor composition is used for enhancing umami, saltiness, sweetness and milk richness of food and drink, the composition may be added in an amount of approximately 0.005% to 1% so that the addition concentration of the compound represented by the formula (1) or a salt thereof to the food or drink product could be, based on the mass of the food or drink product, within a range of 0.1 ppb to 40 ppm, preferably 1 ppb to 10 ppm, more preferably 5 ppb to 2 ppm. As a result, the compound represented by the formula (1) can act on the food or drink product as an active ingredient to thereby enhance the umami, saltiness, sweetness or milk richness of the food or drink product.

When the addition concentration of the compound represented by the formula (1) or a salt thereof to food and drink or to cosmetics is less than 0.1 ppm, the flavor imparting effect thereof to food and drink or to cosmetics and the umami enhancing effect thereof to food and drink would be poor, but when the addition concentration of the compound represented by the formula (1) or a salt thereof to food and drink or to cosmetics is more than 200 ppm, the peculiar flavor of the compound itself would be often unfavorably too strong in food and drink or cosmetics. In addition, there may be an unfavorable probability that the taste balance of food and drink would be lost.

In the flavor composition, any other generally-usable flavor component than the compound represented by the formula (1) or a salt thereof may be incorporated. The other flavor component that can be incorporated in the composition along with the compound represented by the formula (1) or a salt thereof includes various synthetic flavors, natural flavors, natural essential oils, animal or vegetable extracts, etc. As the other flavor components, there may be mentioned synthetic flavors, natural essential oils, natural flavors, animal or vegetable extracts and others described in "Japan Patent Office, Glossary of Well-Known Conventional Techniques (flavors), Part II, Food Flavors, pp. 8-87, published Jan. 14, 2000).

Regarding these components, examples of materials for food flavors (flavor compositions and umami-enhancing flavor compositions) include, as hydrocarbon compounds, monoterpenes such as such as α-pinene, β-pinene, myrcene, camphene, limonene, etc., sesquiterpenes such as valencene, cedrene, caryophyllene, longifolene, etc., 1,3,5-undecatriene, etc.; as alcohol compounds, linear saturated alkanols such as butanol, pentanol, prenol, hexanol, etc., linear unsaturated alcohols such as (Z)-3-hexen-1-ol, 2,6-nonadienol, etc., terpene alcohols such as linalool, geraniol, citronellol, tetrahydromyrcenol, farnesol, nerolidol, cedrol, etc., aromatic alcohols such as benzyl alcohol, phenylethyl alcohol, furfuryl alcohol, etc.; as aldehyde compounds, linear saturated aldehydes such as acetaldehyde, hexanal, decanal, etc., linear unsaturated aldehydes such as (E)-2-hexenal, 2,4-octadienal, etc., terpene aldehydes such as citronellal, citral, etc., aromatic aldehydes such as benzaldehyde, cinnamyl aldehyde, vanillin, ethylvanillin, furfural, heliotropine, etc.; as ketone compounds, linear saturated or unsaturated ketones such as 2-heptanone, 2-undecanone, 1-octen-3-one, etc., linear cyclic diketones such as acetoin, diacetyl, 2,3-pentadione, maltol, ethylmaltol, 2,5-dimethyl-4-hydroxy-3(2H)-furanone, etc., terpene ketones such as hydroxyketone, carvone, menthene, nootkatone, etc., ketones derived from terpene degradation products such as α-ionone, β-ionone, β-damascenone, etc., aromatic ketones such as raspberry ketone, etc.; as furan/ether compounds, cyclic ether such as rose oxide, linalool oxide, menthofuran, theaspirane, etc.; as ester compounds, aliphatic alcohol acetates such as ethyl acetate, isoamyl acetate, etc.; terpene alcohol acetates such as linalyl acetate, geranyl acetate, lavandulyl acetate, etc., fatty acid lower alcohol esters such as ethyl butyrate, ethyl caproate, etc., aromatic esters such as benzyl acetate, methyl salicylate, etc.; as lactone compounds, saturated lactones such as γ-decalactone, γ-dodecalactone, δ-decalactone, δ-dodecalactone, etc., unsaturated lactones such as 7-decen-4-olide, 2-decen-5-olide, etc.; as acid compounds, saturated or unsaturated fatty acids such as butyric acid, octanoic acid, stearic acid, oleic acid, linoleic acid, linolenic acid, etc.; as nitrogen-containing compounds, indole, skatole, pyridine, alkyl-substituted pyradine, methyl anthranilate, etc.: as sulfur-containing compounds, methanethiol, dimethyl sulfide, dimethyl disulfide, allyl isothiocyanate, etc. In addition, as various extracts, there are mentioned herb and spice extracts, coffee, green tea, black tea and oolong tea extracts, milk and milk processed products, and enzymatic decomposition products thereof with lipase, protease, etc.

As materials for umami enhancing flavor compositions, there are further mentioned amino acids such as sodium glutamate, aspartic acid, etc., nucleic acids and salts thereof such as inosinic acid, guanylic acid, adenylic acid, uridylic acid, cytidylic acid, etc., yeast extracts, organic acids such as succinic acid, etc., sugars such as ribose, xylose, arabinose, glucose, fructose, rhamnose, lactose, maltose, sucrose, trehalose, cellobiose, maltotriose, starch syrup, etc., in addition to the above-mentioned materials for food flavors.

Materials for flavors for cosmetics include, in addition to the above-mentioned food flavors, synthetic flavor compounds such as α-amylcinnamyl aldehyde, dihydrojasmone, methylionone, α-damascone, acetylcedrene, methyl dihydrojasmonate, cyclopentadecanolide, etc.; natural essential oils such as sweet orange, bitter orange, petitgrain, lemon, bergamot, mandarin, neroli, peppermint, spearmint, lavender, chamomile, rosemary, eucalyptus, sage, basil, rose, geranium, jasmine, ylang-ylang, anise, clove, ginger, nutmeg, cardamom, Japanese cedar, Japanese cypress, vetiver, patchouli, labdanum, etc.

In the flavor composition, a fixing agent that is ordinarily used in flavor compositions may be incorporated, as needed. The fixing agent includes a solvent such as water, ethanol, etc., as well as ethylene glycol, 1,2-propylene glycol, glycerin, benzyl benzoate, triethyl citrate, Hercolyn, fatty acid triglyceride, fatty acid diglyceride, etc.

Without emulsified, the compound represented by the formula (1) or a salt thereof is, by itself, effective and useful as a flavor modulator, an umami imparting agent, an umami enhancer, a sweetness enhancer, a saltiness enhancer and a milk richness enhancer. By processing the compound represented by the formula (1) or a salt thereof into an emulsified composition or a powdery composition, the dispersibility thereof in water can be improved, and the resultant composition can be readily blended with a food or drink product or with a cosmetic product, and in addition, can change the timing thereof for flavor expression. For example, in the case where the compound represented by the formula (1) or a salt thereof is incorporated in a ramen soup for umami enhancement, and when it is added to an oil-soluble flavor, the oil-soluble flavor will float as oil so that the compound represented by the formula (1) or a salt thereof contained in oil would act in the mouth. On the other hand, when added in the form of an emulsified composition thereof, fine particles of the compound represented by the formula (1) or a salt thereof could uniformly act in the mouth to thereby realize further strengthened and uniform umami enhancement.

An emulsified composition containing the compound represented by the formula (1) or a salt thereof is not specifically limited, and any one prepared by emulsifying the compound represented by the formula (1) or a salt thereof in a known method may be employed here. To the compound represented by the formula (1) or a salt thereof, or to a flavor composition containing it, water that is a component (B) for use in the present invention, one or more selected from sugars, monoalcohols or polyalcohols that is a component (C), and an emulsifier (D) are incorporated, and for example, the resultant composition is mixed, stirred and emulsified using a homo-mixer, a colloid mill, a high-pressure homogenizer or the like to give an emulsified composition.

In emulsifying the above, for example, the compound represented by the formula (1) or a salt thereof is incorporated in an oily phase part, and the component (B) water, and one or more selected from sugars, monoalcohols or polyalcohols as the component (C) are incorporated in an aqueous phase, and the two may be mixed to prepare an oil-in-water emulsion.

Water that is the component (B) for use in the present invention constitutes the above-mentioned aqueous phase along with the component (C) of sugars, monoalcohols or polyalcohols, and the water content in the aqueous phase is generally 50% or less, and is especially preferably in a hydrous state where the content is within a range of about 0 to 25%. When the water content is more than 50%, the composition will lose antiseptic performance.

Sugars, monoalcohols or polyalcohols that are the component (C) in the present invention are incorporated for stabilizing emulsion. Examples of sugars include glucose, fructose, sucrose, trehalose, cellobiose, maltotriose, rhamnose, lactose, maltose, ribose, xylose, arabinose, starch syrup, etc.; examples of monoalcohols include ethanol, propanol, isopropanol, etc.; examples of polyalcohols include glycerin, propylene glycol, 1,3-butylene glycol, sorbitol, maltitol, starch decomposed reduced product, etc.; and a mixture of two or more of these is also employable.

The amount of the aqueous phase to be used in the emulsified composition is generally within a range of about 1 part by weight to about 10 parts by weight relative to one part by weight of the oily phase part, and especially preferably within a range of about 1.5 parts by weight to about 5 parts by weight. As needed, an organic acid such as lactic acid, citric acid, malic acid, tartaric acid or the like may be added to the aqueous phase for the purpose of improving storability.

2-(3-Benzyloxypropyl)pyridine and the above-mentioned various flavors can dissolve in the component (C) of sugars, monoalcohols or polyalcohols in a low concentration, and therefore can be incorporated in the aqueous phase part.

An emulsifier (or a stabilizer as the case may be) of the component (D) for use in the present invention is not specifically limited, and various emulsifiers heretofore used in food and drink and others are usable, and examples thereof include fatty acid monoglyceride, fatty acid diglyceride, fatty acid triglyceride, propylene glycol fatty acid ester, sucrose fatty acid ester, polyglycerin fatty acid ester, (oxidation-processed) lecithin, processed starch, sorbitan fatty acid ester, quillai extract, gum arabic, gum tragacanth, guar gum, karaya gum, xanthane gum, pectine, argic acid and salts thereof, carrageenan, gelatin, casein, etc.

One or more emulsifiers (or stabilizer) are incorporated and, for example, using a homomixer, a colloid mill, a high-pressure homogenizer or the like, the mixture is emulsified to be a form of an emulsified flavor preparation. The amount of the emulsifier (or stabilizer) to be used varies depending on the type of the emulsifier (or stabilizer), but for example, based on the mass of the emulsified flavor preparation, the amount may be within a range of 0.1 to 25% by weight, preferably within a range of 5 to 20% by weight.

Among these emulsifiers, hydrophilic surfactants having HLB of 8 or more are preferred, and in the case, the emulsifier is mixed in the aqueous phase part. Specifically, there are mentioned polyglycerin fatty acid ester, sorbitan fatty acid ester, sucrose fatty acid ester, glycerin fatty acid ester, etc. Examples of polyglycerin fatty acid esters include esters of a polyglycerin having a mean polymerization degree of 3 or more and a fatty acid having 8 or more carbon atoms, for example, decaglycerin monooleate, decaglycerin monostearate, decaglycerin monopalmitate, decaglycerin monomyristate and the like having HLB of about 8 or more, preferably falling within a range of about 8 to about 14.

When polyglycerin fatty acid esters having HLB of lower than 8 are used, in general, it is difficult to prepare emulsified particles having a uniform and small particle size. In addition, the emulsion is unstable, and when it is added to drink, there may be a strong tendency toward a phenomenon of separation such as precipitation, oil separation, etc.

The content of the polyglycerin fatty acid ester to be contained is generally within a range of about 0.05 parts by weight to about 0.5 parts by weight relative to 1 part by weight of the oily phase part, preferably within a range of about 0.15 parts by weight to about 0.3 parts by weight.

One embodiment of a method for preparation of the emulsified composition of the present invention is exemplified below. First, the raw materials for use for the above-mentioned oily phase part are mixed to prepare one part by mass of an oily phase part. Apart from this, about 2 to about 50 parts by weight (water content, about 0.5 to about 10% by weight) of a solution (aqueous phase) is prepared by mixing and dissolving (B) water, (C) one or more selected from sugars, monoalcohols or polyalcohols, and (D) an emulsifier, and the oily phase part and the aqueous phase part are mixed and emulsified using a homomixer, a colloid mill, a high-pressure homogenizer or the like, thereby producing an extremely fine and stable emulsion of fine particles having a particle size of about 0.2 to about 2 μm.

The compound represented by the formula (1) or a salt thereof, or a flavor composition containing it may be contained in the emulsified composition, generally in an amount of, based on the mass of the emulsified composition, 0.1 ppm to 2%, preferably 1 ppm to 0.5%, more preferably 10 ppm to 0.1%.

Further, the emulsified composition may be dried to prepare a powdery composition. For example, an excipient of sugars such as table sugar, lactose, glucose, trehalose, cellobiose, starch syrup, reduced sugar syrup, etc.; sugar alcohols; various starch decomposed products such as dextrin, etc., as well as starch derivatives, starch, gelatin, natural gums such as gum arabic and the like is adequately added to the composition, and then dried according to an adequate drying method of spray drying, vacuum drying, freeze drying or the like to give a form of a powdery composition. The amount of the excipient to be added may be adequately selected depending on the characteristics desired for the powdery composition.

By adding the compound represented by the formula (1) or a salt thereof of the present invention by itself, or by adding the flavor composition containing the compound represented by the formula (1) or a salt thereof as an active ingredient to food or drink products, herbal, green, earthy, almond, nutty or rummy flavor of natural impression of food and drink can be enhanced, and additionally, umami, sweetness, saltiness or milk richness thereof can also be enhanced. Examples of the food or drink products include carbonated drinks such as cola drink, fruit juice-added carbonated drink, milk-added carbonated drink, etc.; soft drinks such as fruit juice drink, vegetable drink, isotonic drink, honey drink, soy milk, vitamin supplement drink, mineral supplement drink, nutrition supplement drink, energy drink, lactobacillus drink, milk drink, etc.; taste-oriented drinks such as green tea, black tea, oolong tea, herb tea, milk tea, coffee, etc.; alcohol drinks such as shochu mixed with soda water, cocktail drink, low-malt beer, fruit liquor, medicinal liquor, etc.; dairy products such as butter, cheese, milk, yoghurt, etc.; desserts such as ice cream, lacto-ice, sherbet, yoghurt, pudding, jelly, dairy dessert, etc., and mixes for producing them; confectionery such as caramel, candy, tablet candy, cracker, biscuit, cookie, pie, chocolate, snack, etc., and mixes such as cake mix and the like for producing them; general foods such as bread, soup, various ready-to-serve foods, etc.; oral compositions such as tooth paste, etc.

By adding 2-(3-benzyloxypropyl)pyridine that is a preferred embodiment of the present invention to food and drink by itself or as a flavor composition containing 2-(3-benzyloxypropyl)pyridine as an active ingredient, herbal, green or nutty flavor of natural impression of food and drink can be enhanced, or umami can be imparted thereto, or umami, sweetness, saltiness or milk richness thereof can be enhanced. Regarding the specific examples of the food or drink products in the case, the same as above shall also apply thereto.

Specific examples of cosmetics whose herbal, earthy, almond, nutty or rummy flavor can be enhanced by adding thereto the compound represented by the formula (1) or a salt thereof of the present invention by itself or in the form of a flavor composition containing the compound represented by the formula (1) or a salt thereof as an active ingredient include perfume; haircare products such as shampoo, hair conditioner, hair cream, pomade, etc.; makeup cosmetics such as face powder, lip rouge, etc.; health and hygiene detergents such as face soap, body soap, laundry soap, laundry detergent, sanitizing detergent, deodorant detergent, etc.; health and hygiene goods such as tooth paste, tissue paper, toilet paper, etc.; aroma products such as in-room aroma, car cologne, etc.

The same as above shall also apply to specific examples of cosmetics whose herbal, green or nutty flavor of natural impression can be enhanced by adding thereto, 2-(3-benzyloxypropyl)pyridine that is one preferred embodiment of the present invention, by itself or in the form of a flavor composition containing 2-(3-benzyloxypropyl)pyridine as an active ingredient.

The present invention is described more specifically with reference to Examples as hereunder.

EXAMPLES

Reaction crude products and purified product in Examples were analyzed using the following analytical instruments.

GC measurement: GC-2014 (manufactured by Shimadzu Corporation) and Chromatopack C-R8A (manufactured by Shimadzu Corporation)

GC column for GC measurement: TC-1 manufactured by GL Sciences (length 30 m, inner diameter 0.53 mm, liquid layer thickness 1.50 μm), TC-1701 manufactured by GL Sciences (length 30 m, inner diameter 0.53 mm, liquid layer thickness 1.00 μm)

GC/MS measurement: 5973 N (manufactured by Agilent Technologies)

GC column for GC/MS measurement: TC-1701 manufactured by GL Sciences (length 30 m, inner diameter 0.25 mm, liquid layer thickness 0.25 μm)

NMR measurement: ECX-400A (manufactured by JEOL Resonance)

Example 1: Preparation of 2-(4-benzyloxybutyl)pyridine 2-(4-Benzyloxybutyl)pyridine is prepared in 5 steps according to the following reaction route.

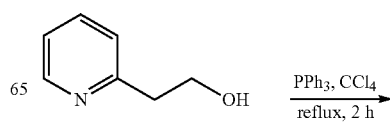

-continued

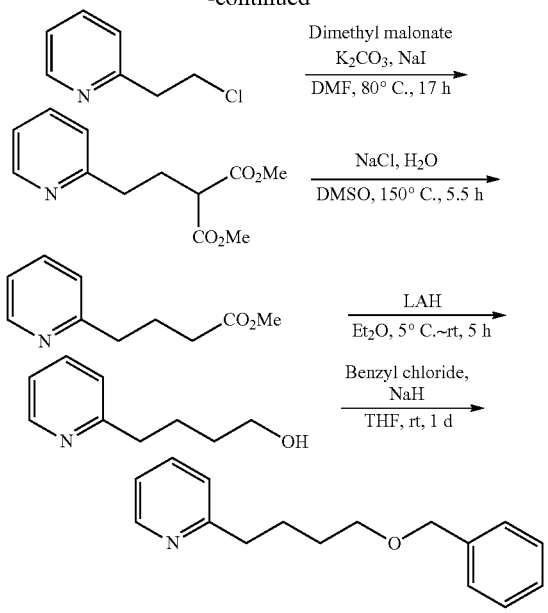

(1) Preparation of 2-(2-chloroethyl)pyridine

2-Pyridine-ethanol (15.00 g, 122 mmol), triphenyl phosphine (38.40 g, 146 mmol) and carbon tetrachloride (100 mL) were put in a 500-mL flask, and heated under reflux. After 1.5 hours, triphenyl phosphine (9.60 g, 36.6 mmol) was added thereto and further heated for 30 minutes under reflux.

The reaction liquid was cooled down to room temperature, and then pentane (200 mL) was added thereto, and filtered using a Kiriyama funnel. The resultant filtrate was concentrated to give a crude product (17.07 g). This was distilled under reduced pressure to give 11.16 g (yield 65.8%, purity 97.1%) of 2-(2-chloroethyl)pyridine.

(2) Preparation of dimethyl 2-(2-pyridyl)ethylmalonate 2-(2-Chloroethyl)pyridine (10.35 g, 73.1 mmol), N,N-dimethylformamide (100 mL), dimethylmalonate (14.48 g, 110 mmol) and potassium carbonate (18.18 g, 132 mmol) were put in a 300-mL flask, and stirred. After 40 minutes, a catalytic amount of sodium iodide (0.25 g) was added thereto, and stirred at 80° C. for 8 hours. Further, dimethyl malonate (9.66 g, 73.1 mmol) was added thereto and stirred at 80° C. for 9 hours, at which the reaction was stopped.

The reaction liquid was cooled down to room temperature, water with ice (300 g) was added thereto, and this was extracted twice with ether, washed with water (200 g), dried and concentrated to give a crude product (20.9 g). This was distilled under reduced pressure to give 7.78 g (yield 44.9%, purity 90.8%) of dimethyl 2-(2-pyridyl)ethylmalonate.

(3) Preparation of methyl 4-(2-pyridyl)butyrate

Dimethyl 2-(2-pyridyl)ethylmalonate (7.72 g, 32.5 mmol), dimethyl sulfoxide (270 mL), water (2.34 g, 130 mmol), and sodium chloride (7.60 g, 130 mmol) were put in a one-L flask, and stirred at 150° C. for 5.5 hours.

The reaction liquid was cooled down to room temperature, and extracted with water (550 mL) and ether (300 mL) added thereto. Further, water (550 mL) was added, and this was extracted with ether (250 mL). Further, a small amount of sodium bicarbonate and edible salt were added thereto until saturation, and this was extracted with ether (250 mL×3 times). The resultant organic layers were combined, washed with 20% saline water (500 mL), dried with magnesium sulfate, and concentrated to give a crude product (5.17 g, purity 82.2%) of methyl 4-(2-pyridyl)butyrate. Not further purified, the crude product was used in the next reaction.

(4) Preparation of 2-pyridine-butanol

In a nitrogen atmosphere, aluminum lithium hydride (0.90 g, 23.7 mmol) and dry ether (20 mL) were put in a 200-mL flask, and stirred at 5° C. in an iced water bath. A dry ether (10 mL) solution of the crude product of methyl 4-(2-pyridyl)butyrate (5.17 g, 28.8 mmol) was dropwise added thereto at 10° C. or lower, and stirred at the same temperature for 2 hours. Further, this was heated up to room temperature and stirred for 3 hours.

A saturated aqueous Rochelle salt solution (100 mL) and ether (20 mL) were added thereto, stirred overnight, and the organic layer was separated. The aqueous layer was extracted with ether (100 mL), and the combined organic layers were washed with 20% saline water (100 mL), dried with sodium sulfate and concentrated to give a crude product (3.98 g). This was distilled under reduced pressure to give 2.14 g (2-stage yield 44.8%, purity 95.8%) of 2-pyridine-butanol.

(5) Preparation of 2-(4-benzyloxybutyl)pyridine

60% sodium hydride (0.47 g, 11.8 mmol) and dry tetrahydrofuran (5 mL) were put into a 200-mL flask, and stirred in a nitrogen atmosphere. In a water bath, a dry tetrahydrofuran (5 mL) solution of 2-pyridine-butanol (1.50 g, 9.92 mmol) was dropwise added thereto at 25° C. or lower, taking 5 minutes, and then stirred at room temperature for 20 minutes. The reactor was again put in a water bath, and a dry tetrahydrofuran (5 mL) solution of benzyl chloride (1.51 g, 11.9 mmol) was dropwise added thereto at 25° C. or lower, taking 15 minutes, and stirred overnight at room temperature.

Cold water (5 mL) was added to the reaction liquid for quenching, and this was extracted with ethyl acetate (30 mL). The resultant organic layer was washed with 20% saline water (30 mL), dried with sodium sulfate and concentrated to give a crude product (2.54 g). This was purified through silica gel chromatography to give 1.04 g (yield 43.4%, purity 98.5%) 2-(4-benzyloxybutyl)pyridine (invention product 1).

Physical Data of 2-(4-benzyloxybutyl)pyridine $^1$H NMR (CDCl$_3$, 400 MHz) δ 1.65-1.73 (m, 2H), 1.79-1.90 (m, 2H), 2.78-2.83 (m, 2H), 3.50 (t, 2H, J=6.4 Hz), 4.49 (s, 2H), 7.07-7.11 (m, 1H), 7.13 (d, 1H, J=8.0 Hz), 7.24-7.30 (m, 1H), 7.32-7.36 (m, 4H), 7.57 (dt, 1H, J=2.0, 7.6 Hz), 8.50-8.53 (m, 1H).

$^{13}$C NMR (CDCl$_3$, 100 MHz) δ 26.43, 29.40, 38.08, 70.18, 72.87, 120.92, 122.73, 127.45, 127.60 (2C), 128.31 (2C), 136.24, 138.57, 149.19, 162.04.

MS (EI, 70 eV) m/z 65 (12), 78 (6), 91 (50), 92 (15), 93 (100), 94 (10), 106 (84), 107 (17), 117 (8), 118 (8), 120 (30), 132 (6), 134 (52), 135 (38), 150 (96), 151 (10).

Example 2: Preparation of 2-(2-phenylethoxyethyl)pyridine 2-(2-Phenylethoxyethyl)pyridine is prepared in a step according to the following reaction route.

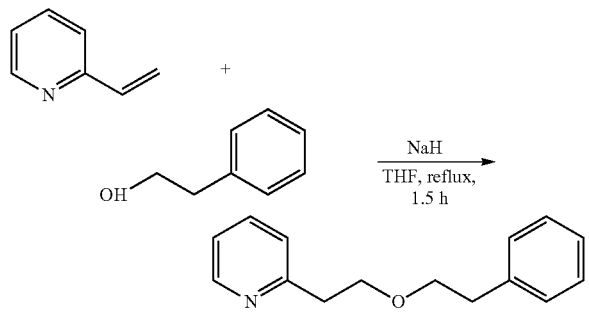

60% sodium hydride (17.09 g, 420 mmol) and dry tetrahydrofuran (400 mL) were put in a one-L flask and stirred in a nitrogen atmosphere. In an ice bath, a dry tetrahydrofuran (50 mL) solution of 2-phenylethyl alcohol (47.48 g, 380 mmol) was dropwise added thereto at 30° C. or lower, taking 20 minutes, and then stirred at room temperature for 10 minutes. The reactor was again put in an ice bath, and a dry tetrahydrofuran (50 mL) solution of 2-vinylpyridine (49.00 g, 460 mmol) was dropwise added thereto at 30° C. or lower, taking 20 minutes, and heated under reflux for 1.5 hours after the addition.

The reaction liquid was cooled, then cold water (300 mL) was added thereto for quenching, and this was extracted with ethyl acetate (200 mL). The resultant organic layer was washed with 20% saline water (300 mL), dried with sodium sulfate and concentrated to give a crude product (139.76 g). This was distilled under reduced pressure to remove a major part of the unreacted raw materials, thereby giving a residue (13.13 g) containing the intended product. The residue was purified through silica gel chromatography to give 910 mg (purity 93.9%) of a fraction containing the intended, high-purity product. Further, this was purified using a Kugelrohr to give 781 mg (yield 0.9%, purity 98.6%) of 2-(2-phenylethoxyethyl)pyridine (invention product 2).

Physical Data of 2-(2-phenylethoxyethyl)pyridine $^1$H NMR (CDCl$_3$, 400 MHz) δ 2.85 (t, 2H, J=6.8 Hz), 3.05 (t, 2H, J=6.4 Hz), 3.66 (t, 2H, J=6.8 Hz), 3.83 (t, 2H, J=6.4 Hz), 7.08-7.12 (m, 1H), 7.13-7.21 (m, 4H), 7.22-7.28 (m, 2H), 7.55 (dt, 1H, J=2.0, 7.6 Hz), 8.50-8.53 (m, 1H).

$^{13}$C NMR (CDCl$_3$, 100 MHz) δ 36.13, 38.58, 70.06, 71.78, 121.23, 123.57, 126.02, 128.20 (2C), 128.83 (2C), 136.17, 138.97, 149.13, 159.20.

MS (EI, 70 eV) m/z 77 (12), 78 (20), 79 (14), 91 (8), 93 (26), 94 (6), 104 (54), 105 (30), 106 (100), 107 (44), 122 (89), 123 (12), 136 (21), 227 (6).

Example 3: Preparation of 2-[3-(p-methoxybenzyloxy)propyl]pyridine

2-[3-(p-methoxybenzyloxy)propyl]pyridine is prepared in a step according to the following reaction route.

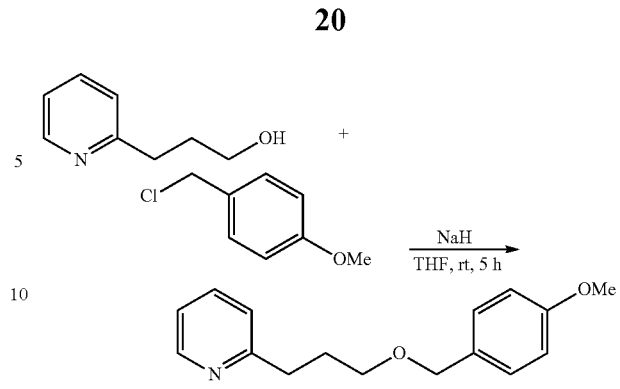

60% sodium hydride (1.75 g, 43.8 mmol) and dry tetrahydrofuran (10 mL) were put into a 200-mL flask, and stirred in a nitrogen atmosphere. In a water bath, a dry tetrahydrofuran (5 mL) solution of 2-pyridine-propanol (5.00 g, 36.4 mmol) was dropwise added thereto at 30° C. or lower, taking 30 minutes, and then stirred at room temperature for 30 minutes. The reactor was again put in a water bath, and a dry tetrahydrofuran (5 mL) solution of p-methoxybenzyl chloride (6.84 g, 43.7 mmol) was dropwise added thereto at 30° C. or lower, taking 30 minutes, and stirred at room temperature for 5 hours.

Cold water (20 mL) was added to the reaction liquid at 30° C. or lower for quenching, and this was extracted with ethyl acetate (50 mL). The resultant organic layer was washed with 20% saline water (50 mL), dried with sodium sulfate and concentrated to give a crude product (11.50 g). This was purified through silica gel chromatography to give 5.78 g (yield 61.7%, purity 99.4%) of 2-[3-(p-methoxybenzyloxy)propyl]pyridine (invention product 3).

Physical Data of 2-[3-(p-methoxybenzyloxy)propyl]pyridine

1H NMR (CDCl$_3$, 400 MHz) δ 2.01-2.08 (m, 2H), 2.86-2.90 (m, 2H), 3.50 (t, 2H, J=6.4 Hz), 3.80 (s, 3H), 4.44 (s, 2H), 6.86-6.89 (m, 2H), 7.07-7.14 (m, 2H), 7.24-7.28 (m, 2H), 7.56 (dt, 1H, J=1.6, 7.6 Hz), 8.50-8.53 (m, 1H).

$^{13}$C NMR (CDCl$_3$, 100 MHz) δ 29.65, 34.85, 55.24, 69.24, 72.46, 113.71 (2C), 120.94, 122.83, 129.21 (2C), 130.63, 136.23, 149.20, 159.07, 161.69.

MS (EI, 70 eV) m/z 92 (5), 93 (100), 94 (8), 106 (6), 121 (39), 136 (14).

Example 4: Preparation of 2-(2-phenylethylthioethyl)pyridine 2-(2-Phenylethylthioethyl)pyridine is prepared in a step according to the following reaction route.

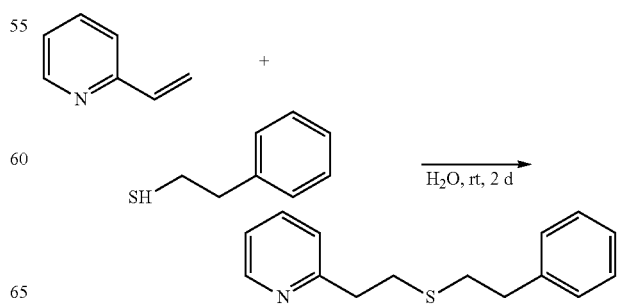

2-Vinylpyridine (5.00 g, 47.6 mmol), 2-phenylethanethiol (6.58 g, 47.6 mmol) and ion-exchanged water (21 mL) were put into a 200-mL flask, and stirred at room temperature for 2 days.

The reaction liquid was extracted with ethyl acetate (50 mL), and the resultant organic layer was washed with 20% saline water (50 mL), dried with sodium sulfate and concentrated to give a crude product (11.37 g). This was purified through silica gel chromatography to give 8.64 g (purity 99.3%) of 2-(2-phenylethylthioethyl)pyridine. A part of this (5.15 g) was further purified using a Kugelrohr to give 5.12 g (yield 74.1%, purity 99.9%) of a high-purity product (invention product 4).

Physical Data of 2-(2-phenylethylthioethyl)pyridine

1H NMR (CDCl$_3$, 400 MHz) δ 2.76-2.82 (m, 2H), 2.84-2.91 (m, 2H), 2.94-2.99 (m, 2H), 3.04-3.10 (m, 2H), 7.12-7.23 (m, 5H), 7.26-7.32 (m, 2H), 7.61 (dt, 1H, J=1.6, 7.6 Hz), 8.53-8.56 (m, 1H).
$^{13}$C NMR (CDCl$_3$, 100 MHz) δ 31.72, 33.70, 36.18, 38.40, 121.41, 123.11, 126.22, 128.36 (2C), 128.40 (2C), 136.31, 140.47, 149.33, 159.95.
MS (EI, 70 eV) m/z 77 (10), 78 (14), 79 (11), 91 (8), 93 (12), 103 (6), 104 (8), 105 (10), 106 (74), 107 (79), 108 (7), 136 (5), 138 (100), 139 (31), 140 (9), 152 (9), 215 (14), 243 (6).

Example 5: Preparation of

2-[3-(p-methylbenzyloxy)propyl]pyridine 2-[3-(p-methylbenzyloxy)propyl]pyridine is produced in a process according to the following reaction route.

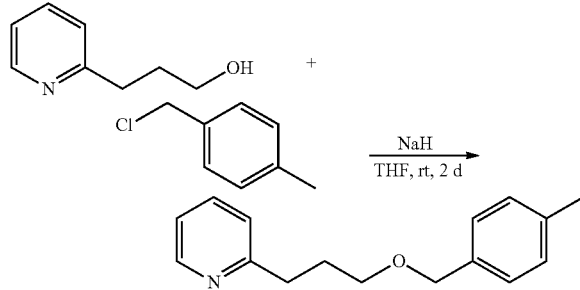

60% sodium hydride (1.75 g, 43.8 mmol), and dry tetrahydrofuran (10 mL) were put into a 200-mL flask, and stirred in a nitrogen atmosphere. In a water bath, a dry tetrahydrofuran (5 mL) solution of 2-pyridine-propanol (5.05 g, 36.8 mmol) was dropwise added thereto at 30° C. or lower, taking 30 minutes, and then stirred at room temperature for 30 minutes. The reactor was again put in a water bath, and a dry tetrahydrofuran (5 mL) solution of p-methylbenzyl chloride (6.20 g, 44.1 mmol) was dropwise added thereto at 30° C. or lower, taking 30 minutes, and stirred at room temperature for 2 days.

Cold water (20 mL) was put into the reaction liquid at 30° C. or lower for quenching, and this was extracted with ethyl acetate (50 mL). The resultant organic layer was washed with 20% saline water (50 mL), dried with sodium sulfate and concentrated to give a crude product (10.13 g). This was purified through silica gel chromatography to give 4.36 g (yield 49.1%, purity 99.7%) of 2-[3-(p-methylbenzyloxy)propyl]pyridine (invention product 5).

Physical Data of 2-[3-(p-methylbenzyloxy)propyl]pyridine

1H NMR (CDCl$_3$, 400 MHz) δ 2.01-2.09 (m, 2H), 2.34 (s, 3H), 2.86-2.91 (m, 2H), 3.51 (t, 2H, J=6.4 Hz), 4.46 (s, 2H), 7.07-7.12 (m, 2H), 7.15 (d, 2H, J=8.0 Hz), 7.23 (d, 2H, J=8.0 Hz), 7.56 (dt, 1H, J=2.0, 7.6 Hz), 8.50-8.53 (m, 1H).
$^{13}$C NMR (CDCl$_3$, 100 MHz) δ 21.12, 29.67, 34.86, 69.37, 72.69, 120.94, 122.84, 127.72 (2C), 128.98 (2C), 135.47, 136.22, 137.14, 149.21, 161.72.
MS (EI, 70 eV) m/z 77 (8), 78 (6), 79 (7), 92 (9), 93 (100), 94 (11), 103 (5), 105 (26), 106 (14), 120 (11), 121 (25), 136 (55), 137 (5).

Example 6: Preparation of

2-[3-(2,5-dimethylbenzyloxy)propyl]pyridine 2-[3-(2,5-Dimethylbenzyloxy)propyl]pyridine is prepared in a step according to the following reaction route.

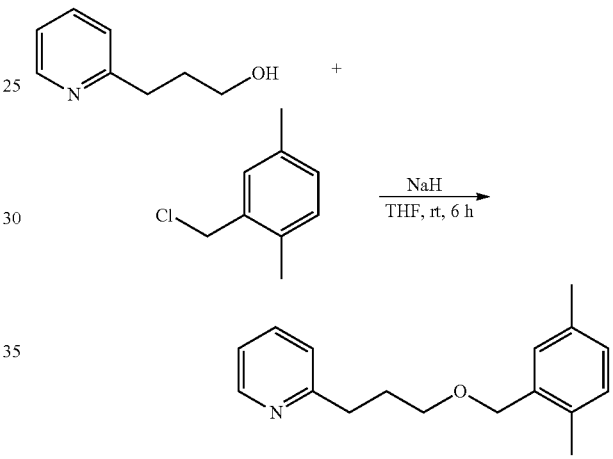

60% sodium hydride (1.75 g, 43.8 mmol) and dry tetrahydrofuran (10 mL) were put in a 200-mL flask and stirred in a nitrogen atmosphere. In a water bath, a dry tetrahydrofuran (5 mL) solution of 2-pyridine-propanol (5.00 g, 36.4 mmol) was dropwise added thereto at 35° C. or lower, taking 20 minutes, and then stirred at room temperature for 40 minutes. The reactor was again put in a water bath, and a dry tetrahydrofuran (5 mL) solution of 2,5-dimethylbenzyl chloride (6.76 g, 43.7 mmol) was dropwise added thereto at 30° C. or lower, taking 10 minutes, and stirred at room temperature for 6 hours.

Cold water (30 mL) was added to the reaction liquid at 35° C. or lower for quenching, and this was extracted with ethyl acetate (50 mL). The resultant organic layer was washed with 20% saline water (50 mL), dried with sodium sulfate and concentrated to give a crude product (12.06 g). This was purified through silica gel chromatography to give 5.62 g (yield 60.5%, purity 99.1%) of 2-[3-(2,5-dimethylbenzyloxy)propyl]pyridine (invention product 6).

Physical Data of 2-[3-(2,5-dimethylbenzyloxy)propyl]pyridine

1H NMR (CDCl$_3$, 400 MHz) δ 2.03-2.11 (m, 2H), 2.29 (s, 3H), 2.31 (s, 3H), 2.86-2.92 (m, 2H), 3.55 (t, 2H, J=6.4 Hz), 4.46 (s, 2H), 6.98-7.14 (m, 5H), 7.56 (dt, 1H, J=1.6, 7.6 Hz), 8.51-8.53 (m, 1H).

$^{13}$C NMR (CDCl$_3$, 100 MHz) δ 18.30, 20.92, 29.71, 34.91, 69.74, 71.30, 120.96, 122.85, 128.27, 129.25, 130.07, 133.37, 135.12, 136.12, 136.25, 149.20, 161.70.

MS (EI, 70 eV) m/z 91 (9), 92 (7), 93 (100), 94 (8), 106 (9), 117 (11), 118 (36), 119 (20), 120 (10), 121 (26), 136 (38), 196 (8).

Comparative Example 1: Preparation of 2-(2-benzyloxyethyl)pyridine

An aqueous 25 wt % sodium hydroxide solution (120.0 g, 750 mmol), 2-pyridine-ethanol (12.34 g, 100 mmol), benzyl chloride (15.51 g, 123 mmol) and tetra-n-butylammonium bromide (1.61 g, 4.99 mmol) were put into a 300-mL flask, stirred at 45° C. for 3 hours, and the reaction liquid was extracted with hexane (100 mL). The organic layer was washed with 20% saline water (100 mL), and the product was formed into a hydrochloride thereof with 2 mol/L hydrochloric acid (100 mL) and extracted in an aqueous layer, and then an aqueous saturated sodium carbonate solution (150 mL) was added to the aqueous layer to make it alkaline. The aqueous layer containing the intended product was extracted with ethyl acetate (100 mL×once, 50 mL×once). The resultant organic layers were combined, washed with 20% saline water (100 mL), the organic layer was dewatered and dried with anhydrous sodium sulfate, ethyl acetate was recovered under reduced pressure to give a concentrated product (22.75 g). The concentrated product was purified through distillation under reduced pressure to give 2-(2-benzyloxyethyl)pyridine (16.51 g, yield 77.4%, purity 99.9%) (comparative product 1).

Physical Data of 2-(2-benzyloxyethyl)pyridine

1H NMR (400 MHz, CDCl$_3$) δ 3.11 (t, 2H, J=6.8 Hz), 3.86 (t, 2H, J=6.8 Hz), 4.53 (s, 2H), 7.12 (dd, 1H, J=7.6, 5.2 Hz), 7.22 (d, 1H, J=7.6 Hz), 7.24-7.33 (m, 5H), 7.60 (dt, 1H, J=1.2, 7.6 Hz), 8.53 (dm, 1H, J=5.2 Hz).

$^{13}$C NMR (100 MHz, CDCl$_3$) δ 38.71, 69.59, 72.95, 121.31, 123.59, 127.50, 127.58 (2C), 128.31 (2C), 136.23, 138.35, 149.26, 159.20.

MS (EI, 70 eV) m/z 39 (10), 51 (12), 65 (27), 78 (12), 79 (13), 91 (75), 92 (10), 93 (24), 106 (61), 107 (100), 122 (71), 168 (2), 182 (6).

Example 7: Evaluation of Flavor of Invention Products 1 to 6

A 1% ethanol solution of the invention products 1 to 6 prepared in Examples 1 to 6 was prepared as an evaluation solution. The evaluation solution was prepared in a sample bottle. Regarding the flavor of the sample smelling from the bottle mouth and the flavor of a flavor paper prepared by infiltrating the evaluation solution into a paper, well-trained 5 panelists tested the solution for flavor evaluation. A typical evaluation of each product is shown in Table 1.

TABLE 1

| Compound | Flavor Evaluation |
| --- | --- |
| 2-(4-benzyloxybutyl)pyridine (invention product 1) | Earthy |
| 2-(2-phenylethoxyethyl)pyridine (invention product 2) | Earthy, hyacinthine |
| 2-[3-(p-methoxybenzyloxy)propyl]pyridine (invention product 3) | Bitter almond |
| 2-(2-phenylethylthioethyl)pyridine (invention product 4) | Metallic spicy savor |

TABLE 1-continued

| Compound | Flavor Evaluation |
| --- | --- |
| 2-[3-(p-methylbenzyloxy)Propyl]pyridine (invention product 5) | Nutty |
| 2-[3-(2,5-dimethylbenzyloxy)propyl]pyridine (invention product 6) | Rummy |

Example 8: Pineapple-Like Compounded Flavor Composition

According to the formulation of the following Table 2, a pineapple-like compounded flavor composition was formulated to be a comparative product 2.

TABLE 2

| | | |
| --- | --- | --- |
| Ethyl acetate | 12 | part by mass |
| Ethyl butyrate | 10 | " |
| Isoamyl acetate | 4 | " |
| Isoamyl valerate | 2.2 | " |
| Isobutyric acid | 2.8 | " |
| Isovaleric acid | 1.2 | " |
| Allyl caproate | 1.4 | " |
| Ethyl caproate | 0.8 | " |
| Ethyl caprylate | 0.6 | " |
| Ethyl caprate | 0.8 | " |
| Isoamyl alcohol | 1.4 | " |
| Diethyl malonate | 1.2 | " |
| Citral | 0.6 | " |
| Linalool | 0.2 | " |
| Maltol | 0.8 | " |
| Propylene glycol | 500 | " |
| 95% ethanol | 460 | " |
| Total | 1000 | |

0.2 g (0.02% by mass) of any of the invention products 1 to 6 was mixed in 999.8 g of the above-mentioned, pineapple-like compounded flavor composition (comparative product 2) to prepare a novel pineapple-like compounded flavor composition. One prepared by mixing the invention product 1 in the comparative product 2 was referred to as an invention product 7, one prepared by mixing the invention product 2 in the comparative product 2 was referred to as an invention product 8, one prepared by mixing the invention product 3 in the comparative product 2 was referred to as an invention product 9, one prepared by mixing the invention product 4 in the comparative product 2 was referred to as an invention product 10, one prepared by mixing the invention product 5 in the comparative product 2 was referred to as an invention product 11, and one prepared by mixing the invention product 6 in the comparative product 2 was referred to as an invention product 12. Five expert panelists compared the invention products 7 to 12 with the comparative product 2. For flavor evaluation, 10 ml of the flavor composition was prepared in a sample bottle (30 ml). Well-trained five panelists evaluated the flavor smelling from the bottle mouth and the flavor of the flavor paper prepared by infiltrating the flavor composition into a paper. As a result, all of the five expert panelists concluded that the invention products 7 to 12 all had fresher and better pineapple characteristics of natural impression than the comparative product 2 and were all remarkably more excellent than the latter in point of the flavor durability.

Example 9: Incorporation of Pineapple-Like Compounded Flavor Composition in Sherbet The pineapple-like compounded flavor composition (comparative product 2 or invention product 7) obtained in Example 8 was added to sherbet having the following formulation to prepare sherbet according to an ordinary method, and well-trained 5 panelists ate it for organoleptic evaluation.

Sherbet Compounding Formulation (Part by Mass)

Sugar: 10, starch syrup (75%): 6, fructose sucrose liquid sugar syrup (75%): 5, citric acid (crystal): 0.1, 20% pineapple juice: 10, invention product 7 (or comparative product 2): 0.2, water to make a total amount of 100.

Five panelists ate these sherbet products for organoleptic evaluation. As a result, all the five panelists concluded that the sherbet added with the invention product 7 had fresher and better pineapple characteristics of natural impression than the sherbet added with comparative product 2, and evaluated that, regarding the taste thereof, the former realized better umami and sweetness than the latter.

Example 10: Lilac-Type Compounded Flavor Composition

According to the formulation of the following Table 3, a lilac-type compounded flavor composition was prepared to be a comparative product 3.

TABLE 3

| | | |
|---|---|---|
| Phenylethyl acetate | 4 | part by mass |
| Cinnamic alcohol | 16 | " |
| Terpineol | 52 | " |
| Cyclamen aldehyde | 4 | " |
| Heliotropine | 20 | " |
| Cinnamyl acetate | 4 | " |
| Carnation absolute | 8 | " |
| Linalool | 12 | " |
| Indole | 0.8 | " |
| Styrax resinoid | 12 | " |
| Ylang-ylang | 4 | " |
| Hydroxycitronellal | 116 | " |
| Benzyl acetate | 8 | " |
| Anisaldehyde | 8 | " |
| Absolute jasmine | 8 | " |
| Phenylethyl alcohol | 111.2 | " |
| Anise alcohol | 12 | " |
| 1,3-butylene glycol | 600 | " |
| Total | 1000 | |

0.2 g (1% by mass) of any of the invention products 1 to 6 was mixed in 99.8 g of the above-mentioned lilac-type flavor composition (comparative product 3) to prepare a novel lilac-type compounded flavor composition. One prepared by mixing the invention product 1 in the comparative product 3 was referred to as an invention product 13; one prepared by mixing the invention product 2 in the comparative product 3 was referred to as an invention product 14; one prepared by mixing the invention product 3 in the comparative product 3 was referred to as an invention product 15; one prepared by mixing the invention product 4 in the comparative product 3 was referred to as an invention product 16; one prepared by mixing the invention product 5 in the comparative product 3 was referred to as an invention product 17; one prepared by mixing the invention product 6 in the comparative product 3 was referred to as an invention product 18. Five panelists compared the invention products 13 to 18 with the comparative product 3. As a result, all the panelists concluded that the invention products 13 to 18 all had fresher lilac characteristics of natural impression than the comparative product 3 and were all remarkably more excellent than the latter in point of the flavor durability.

Example 11: Incorporation of Lilac-Type Compounded Flavor Composition in Shampoo The lilac-type compounded flavor composition (comparative product 3 or invention product 13) obtained in Example 10 was added to shampoo having the following formulation to prepare shampoo according to an ordinary method, and well-trained 5 panelists tried it in shampooing for organoleptic evaluation.

Shampoo Formulation (Part by Mass)

Sodium polyoxyethylene laurylsulfate: 20, coconut oil fatty acid diethanolamide: 5, glycerin: 4, invention product 13 (or comparative product 3); 0.2, water to make a total amount of 100.

Five panelists tested these shampoo products for organoleptic evaluation. As a result, all the five panelists concluded that the shampoo added with the invention product 13 had fresher and better lilac characteristics of natural impression than the shampoo added with the comparative product 3.

Example 12: Confirmation of Umami

A solution was prepared by dissolving any of the invention products 1 to 6 in water to have a concentration shown in Table 4. As a comparative product, a solution was prepared by dissolving the comparative product 1 (2-(2-benzyloxyethyl)pyridine) to have the same concentration. Water with no addition was prepared as a control product. Well-trained 10 panelists tasted the solutions prepared by dissolving any the invention products 1 to 6 and the comparative product 1 for organoleptic evaluation of umami.

Umami evaluation was based on the control product of water. Each sample was given any of a point 0, no difference from control; 1, somewhat stronger than control; 2, stronger than control; 3, considerably stronger than control; and 4, poor taste balance. An average point given by those 10 panelists is shown in Table 4.

TABLE 4

| Addition Concentration | Invention Product 1 | Invention Product 2 | Invention Product 3 | Invention Product 4 | Invention Product 5 | Invention Product 6 | Comparative Product 1 |
|---|---|---|---|---|---|---|---|
| 2 ppb | 0.0 | 0.0 | 0.0 | 0.0 | 0.0 | 0.0 | 0.0 |
| 10 ppb | 0.8 | 0.7 | 0.8 | 0.7 | 0.6 | 0.5 | 0.1 |
| 0.1 ppm | 1.6 | 1.5 | 1.4 | 1.6 | 1.4 | 1.2 | 0.8 |
| 1 ppm | 2.3 | 2.0 | 2.1 | 2.2 | 2.0 | 2.0 | 1.5 |
| 20 ppm | 2.9 | 2.8 | 2.8 | 3.0 | 2.7 | 2.6 | 2.2 |
| 200 ppm | 3.4 | 3.2 | 3.0 | 3.6 | 3.1 | 3.0 | 2.8 |
| 500 ppm | 3.8 | 3.8 | 3.6 | 3.9 | 3.6 | 3.6 | 3.3 |
| 2000 ppm | 4.0 | 4.0 | 3.9 | 4.0 | 3.9 | 3.9 | 3.8 |

As shown in Table 4, the aqueous solutions prepared by dissolving any of the invention products 1 to 6 alone in water had umami. It is known that the solutions provided umami when the concentration of the product therein fell within a range of 0.01 ppm to 200 ppm by mass, and in particular, provided good umami when the concentration was 0.1 ppm to 20 ppm or so.

On the other hand, the aqueous solution prepared by dissolving the comparative product 1 alone in water also had umami. It is known that the solution provided umami when the concentration fell within a range of 0.1 ppm to 2000 ppm by mass, and in particular, provided good umami when the concentration was 1 ppm to 200 ppm or so.

Specifically, it is recognized that the umami imparting effect of the invention products 1 to 6 is stronger by 10 times or so than the comparative product 1, and the concentration of the invention products 1 to 6 to provide the same umami intensity was about 1/10 that of the comparative product 1.

Example 13: Confirmation of Umami Imparting and Saltiness Enhancing Effect

An aqueous 0.3 mass % sodium chloride solution (control), and solutions of the invention products 1 to 6 each dissolved in a 0.3 mass % sodium chloride solution to have the concentration shown in Table 5 were prepared. As a comparative product, a solution was prepared by dissolving the comparative product 1 in 0.3 mass % sodium chloride. Well-trained 10 panelists tasted the solutions for organoleptic evaluation of umami impartment and saltiness enhancement.

Umami and saltiness scores are as follows, based on the aqueous 0.3 mass % sodium chloride solution as a control. Each sample was given any of a point 0, no change from control; 1, slightly higher umami and saltiness than control; 2, higher umami and saltiness than control; 3, considerably higher umami and saltiness than control; 4, extremely higher umami and saltiness than control; and 5, bitter as lacking balance of umami and saltiness. An average point given by those 10 panelists is shown in Table 5.

TABLE 5

| Addition Concentration | Invention Product 1 | Invention Product 2 | Invention Product 3 | Invention Product 4 | Invention Product 5 | Invention Product 6 | Comparative Product 1 |
| --- | --- | --- | --- | --- | --- | --- | --- |
| 0.05 ppb | 0.0 | 0.0 | 0.0 | 0.0 | 0.0 | 0.0 | 0.0 |
| 0.1 ppb | 0.8 | 0.7 | 0.8 | 0.6 | 0.8 | 0.5 | 0.0 |
| 1 ppb | 1.4 | 1.5 | 1.6 | 1.8 | 1.5 | 1.3 | 0.6 |
| 10 ppb | 2.3 | 2.4 | 2.6 | 2.3 | 2.2 | 2.0 | 1.5 |
| 0.1 ppm | 3.2 | 3.0 | 3.3 | 3.4 | 3.0 | 2.9 | 2.1 |
| 0.5 ppm | 3.7 | 3.9 | 3.5 | 3.8 | 3.6 | 3.5 | 3.0 |
| 2 ppm | 4.3 | 4.4 | 4.2 | 4.5 | 4.2 | 4.1 | 3.4 |
| 10 ppm | 4.7 | 4.6 | 4.8 | 4.8 | 4.6 | 4.6 | 4.2 |
| 50 ppm | 4.9 | 5.0 | 4.9 | 5.0 | 4.8 | 4.8 | 4.8 |

As shown in Table 5, the aqueous solutions prepared by dissolving any of the invention products 1 to 6 in an aqueous 0.3 mass % sodium chloride solution had umami and salty taste, and they provided umami at a lower concentration than that of the solutions prepared by dissolving the invention products 1 to 6 in water in Example 12. Accordingly, the concentration of the invention products 1 to 6 capable of realizing umami impartation and saltiness enhancement when combined with edible salt is considered to be within a range of 0.1 ppb to 2 ppm by mass, preferably 1 ppb to 0.5 ppm. In addition, it is recognized that the umami imparting effect of the invention products 1 to 6 is higher by about 10 times than that of the comparative product 1, and the concentration of the invention products 1 to 6 to realize the same degree of umami intensity is about 1/10 that of the comparative compound 1.

Example 14: Confirmation of Umami and Saltiness Enhancement

Well-trained 5 panelists tasted an aqueous solution of 0.3 mass % edible salt and 0.03 mass % sodium glutamate (MSG), and aqueous solutions prepared by adding to the aqueous solution, 10 ppb of any of the invention products 1 to 6, for organoleptic evaluation in point of umami and saltiness enhancement. As a result, all the five panelists concluded that the aqueous solutions added with the invention products 1 to 6 gave stronger umami and saltiness than the aqueous solution of 0.3 mass % edible salt and 0.03 mass % sodium glutamate (MSG).

Example 15: Confirmation of Umami Enhancing Effect

Well-trained 5 panelists tasted an aqueous solution of 0.1 mass % sodium inosinate (5'-IMP.2Na), and aqueous solutions prepared by adding to the aqueous 0.1 mass % sodium inosinate solution, 10 ppb of any of the invention products 1 to 6, for organoleptic evaluation in point of umami. As a result, all the five panelists concluded that the aqueous solutions added with 10 ppb of the invention products 1 to 6 gave stronger umami than the aqueous 0.1 mass % sodium inosinate solution.

Example 16: Confirmation of Sweetness Enhancing Effect

Well-trained 5 panelists tasted an aqueous 3 mass % sucrose solution, and aqueous solutions prepared by adding to the aqueous 3 mass % sucrose solution, 5 ppb of any of the invention products 1 to 6, for organoleptic evaluation in point of sweetness. As a result, all the five panelists concluded that the aqueous solutions added with 5 ppb of the invention products 1 to 6 gave stronger sweetness than the aqueous 3 mass % sucrose solution.

Example 17: Addition to Soup Broth for Udon Noodle 0.05 ppm of any of the invention products 1 to 6 was added to commercially-available soup broth for udon noodle (tripe strength). 200 ml of hot water was added to 100 ml of each of the added soup broth and the non-added soup broth, and well-trained 5 panelists tasted them for organoleptic evaluation in point of umami. As a result, all the five panelists concluded that the soup broth added with 0.05 ppm of the invention products 1 to 6 provided stronger umami, saltiness and sweetness than the non-added, commercial soup broth.

Example 18: Addition of Katsuobushi-Like Compounded Flavor Composition to Mentsuyu (Soup Broth for Noodle)

According to the formulation of the following Table 6, a katsuobushi-like compounded flavor composition (a type that imparts umami in addition to flavor) was prepared.

TABLE 6

| 1,2,3-trimethoxy-5-methylbenzene | 40 | part by mass |
|---|---|---|
| Isosafrole | 2 | " |
| 2-penten-1-ol | 8 | " |
| Trans-2-pentenal | 1 | " |
| Cyclotene | 10 | " |
| Diacetyl | 5 | " |
| 2-methylfuran | 20 | " |
| Acetic acid | 3 | " |
| γ-butyrolactone | 1 | " |
| (E,Z,Z)-2,4,7-tridecatrienal | 0.00005 | " |
| 4,7-tridecadienal | 0.00005 | " |
| Trimethylamine | 0.00001 | " |
| 2-methylfuran-3-thiol | 0.00005 | " |
| 2-(4-benzyloxybutyl)pyridine (invention product 1) | 1 | " |
| 95% ethanol | 100 | " |
| Propylene glycol | balance | " |
| Total | 1000 | |

According to the formulation of the following Table 7, mentsuyu was prepared, and 0.02% of the katsuobushi-like compounded flavor composition of Table 6 was added thereto.

TABLE 7

| Soy sauce | 500 | Part by mass |
|---|---|---|
| Mirin (sweet cooking rice wine) | 200 | " |
| Sugar | 100 | " |
| Yeast extract | 6 | " |
| Water | 194 | " |
| Total | 1000 | |

Well-trained 5 panelists tasted the mentsuyu not added with the katsuobushi-like compounded flavor composition and the katsuobushi-like compounded flavor composition-added mentsuyu for organoleptic evaluation. As a result, all the five panelists concluded that the mentsuyu added with the katsuobushi-like compounded flavor composition containing the invention product 1 was better as given a katsuobushi-like flavor than the non-added mentsuyu, additionally saying that the former was better as given enhanced umami, saltiness and sweetness.

Example 19: Katsuobushi-Like Emulsified Flavor Composition 100 g of the katsuobushi-like compounded flavor composition of Table 6 as an oily phase, and a solution of 312.5 g of glycerin, 65 g of ion-exchanged water and 22.5 g of decaglycerin monostearate as an aqueous phase were prepared. The two were mixed by stirring with a TK-homogenizer (manufactured by Primix Corporation) at 8000 rpm for 10 minutes for emulsification. Thus, a katsuobushi-like emulsified flavor composition in the form of an O/W emulsion was prepared, whose absorbance at a wavelength 680 nm in 1/2000 dilution with ion-exchanged water was 0.2 Abs. This is an invention product 19 (having a 2-(4-benzyloxybutyl)pyridine concentration of 0.2% by mass).

Example 20: Addition of Katsuobushi-Like Emulsified Flavor Composition to Mentsuyu Mentsuyu was prepared according to the formulation of the above Table 7, and 0.01% of the invention product 19, katsuobushi-like emulsified flavor composition was added thereto (2-(4-benzyloxybutyl)pyridine concentration 0.2 ppm).

Well-trained 5 panelists tasted the mentsuyu not added with the katsuobushi-like emulsified flavor composition and the katsuobushi-like emulsified flavor composition-added mentsuyu for organoleptic evaluation. As a result, all the five panelists concluded that the mentsuyu added with the katsuobushi-like emulsified flavor composition of the invention product 19 was better as given a katsuobushi-like flavor, additionally saying that the composition-added mentsuyu was an extremely better-tasting one as given greatly enhanced umami, saltiness and sweetness.

Example 21: Katsuobushi-Like Powdery Flavor Composition 70 g of gum arabic and 20 g of trehalose were dissolved in 150 g of water to be an aqueous phase, sterilized by heating at 85 to 90° C. for 15 minutes, and then cooled down to 40° C. As an oily phase, 10 g of the katsuobushi-like compounded flavor composition of Table 6 was added thereto and mixed, and then emulsified with a TK-homomixer to give an O/W emulsified composition. The emulsified composition was spray-dried, using a mobile minor spray drier by Niro, at an inlet temperature of 140° C. and an outlet temperature of 75° C. to produce 95 g of a katsuobushi-like powdery flavor composition (invention product 20: 2-(4-benzyloxybutyl)pyridine concentration 0.1% by mass).

Example 22: Addition of Katsuobushi-Like Powdery Flavor Composition to Powdery Ramen Soup Powdery ramen soup was prepared according to the formulation of Table 8. 1% by mass of the invention product 20 was further added thereto.

TABLE 8

| | Amount Added (part by mass) |
|---|---|
| Edible salt | 360 |
| Powdered soy sauce | 220 |
| Sodium L-glutamate | 120 |
| Meat extract powder | 100 |
| Sugar | 80 |
| Seafood extract powder | 30 |
| Vegetable extract powder | 20 |
| Spice powder | 10 |
| Sodium succinate | 5 |
| Dextrin | 55 |
| Total | 1000 |

Powdery ramen soup added with the katsuobushi-like powdery flavor composition of the invention product 20 and that not added with it were prepared each in an amount of 10 g, 600 ml/one of hot water (70° C.) was added to dilute them, and well-trained 5 panelists tasted them for organoleptic evaluation. As a result, all the five panelists concluded that the ramen soup added with the katsuobushi-like powdery flavor composition of the invention product 20 was better as given a katsuobushi-like flavor, additionally saying that the composition-added ramen soup was an extremely better-tasting one as given greatly enhanced umami, saltiness and sweetness.

Example 23: Milk-Like Compounded Flavor Composition (a Type that Imparts Richness in Addition to Flavor)

According to the formulation of the following Table 9, a milk-like compounded flavor composition (comparative product 4) was prepared.

TABLE 9

| | | |
|---|---|---|
| Vanillin | 25.0 | part by mass |
| Ethylvanillin | 35.0 | " |
| Maple lactone | 2.5 | " |
| Ethylmaltol | 3.5 | " |
| γ-undecalactone | 2.0 | " |
| γ-nonalactone | 10.0 | " |
| δ-decalactone | 2.5 | " |
| Acetylmethylcarbinol | 3.0 | " |
| Diacetyl | 7.0 | " |
| Butyric acid | 5.0 | " |
| Propylene glycol | 904.5 | " |
| Total | 1000.0 | " |

One mg (10 ppm) of any of the invention products 1 to 6 was mixed in 100 g of the milk-like compounded flavor composition (comparative product 4) to prepare a novel milk-like compounded flavor composition. One prepared by mixing the invention product 1 in the comparative product 4 was referred to as a milk-like compounded flavor composition of an invention product 21; one prepared by mixing the invention product 2 in the comparative product 4 was referred to as that of an invention product 22; one prepared by mixing the invention product 3 in the comparative product 4 was referred to as that of an invention product 23; one prepared by mixing the invention product 4 in the comparative product 4 was referred to as that of an invention product 24; one prepared by mixing the invention product 5 in the comparative product 4 was referred to as that of a milk-like compounded flavor composition of an invention product 25; and one prepared by mixing the invention product 6 in the comparative product 4 was referred to as that of an invention product 26.

Example 24: Addition to Aqueous Solution of Skim Milk

A mixed solution (aqueous solution of skin milk) of 10 parts by mass of commercial skim milk and 90 parts by mass of water was prepared, and 0.1% of the milk-like compounded flavor composition prepared in Example 23 was added thereto. Well-trained 5 panelists tasted the aqueous solution of skim milk not added with the milk-like compounded flavor composition, and the aqueous solution of skim milk added with 0.1% by mass of any of the comparative product 4 and the invention products 21 to 26 for organoleptic evaluation. As a result, all the five panelists concluded that the aqueous solution of skim milk added with the comparative product 4 was better-tasting than the non-added aqueous solution of skim milk as given enriched milk flavor, further saying that the aqueous solutions of skim milk added with any of the invention products 21 to 26 were as a whole extremely better than the aqueous solution of skim milk added with the comparative product 4 as given stronger umami and sweetness and further given stronger milk richness, that is, the taste of the former was extremely good as a whole.

Example 25: Milk-Like Emulsified Flavor Composition

According to the formulation of the following Table 10, milk-like compounded flavor compositions (reference products 1 to 7) were prepared.

TABLE 10

| | Milk-like Compounded Flavor Composition (part by mass) | | | | | | |
|---|---|---|---|---|---|---|---|
| | Reference Product 1 | Reference Product 2 | Reference Product 3 | Reference Product 4 | Reference Product 5 | Reference Product 6 | Reference Product 7 |
| Vanillin | 25.0 | 25.0 | 25.0 | 25.0 | 25.0 | 25.0 | 25.0 |
| Ethylvanillin | 35.0 | 35.0 | 35.0 | 35.0 | 35.0 | 35.0 | 35.0 |
| Maple lactone | 2.5 | 2.5 | 2.5 | 2.5 | 2.5 | 2.5 | 2.5 |
| Ethyl maltol | 3.5 | 3.5 | 3.5 | 3.5 | 3.5 | 3.5 | 3.5 |
| γ-undecalactone | 2.0 | 2.0 | 2.0 | 2.0 | 2.0 | 2.0 | 2.0 |
| γ-nonalactone | 10.0 | 10.0 | 10.0 | 10.0 | 10.0 | 10.0 | 10.0 |
| δ-decalactone | 2.5 | 2.5 | 2.5 | 2.5 | 2.5 | 2.5 | 2.5 |
| Acetylmethylcarbinol | 3.0 | 3.0 | 3.0 | 3.0 | 3.0 | 3.0 | 3.0 |
| Diacetyl | 7.0 | 7.0 | 7.0 | 7.0 | 7.0 | 7.0 | 7.0 |
| Butyric acid | 5.0 | 5.0 | 5.0 | 5.0 | 5.0 | 5.0 | 5.0 |
| Invention product 1 | — | 10.0 | — | — | — | — | — |
| Invention product 2 | — | — | 10.0 | — | — | — | — |
| Invention product 3 | — | — | — | 10.0 | — | — | — |
| Invention product 4 | — | — | — | — | 10.0 | — | — |
| Invention product 5 | — | — | — | — | — | 10.0 | — |
| Invention product 6 | — | — | — | — | — | — | 10.0 |
| Middle chain fatty acid triglyceride | balance | balance | balance | balance | balance | balance | balance |
| Total | 1000.0 | 1000.0 | 1000.0 | 1000.0 | 1000.0 | 1000.0 | 1000.0 |

100 g of any of the milk-like compounded flavor compositions (reference products 1 to 7) of Table 10 as an oily phase, and a solution of 312.5 g of glycerin, 65 g of ion-exchanged water and 22.5 g of decaglycerin monopalmitate as an aqueous phase were prepared. The two liquids were mixed by stirring with a TK-homogenizer (manufactured by Primix Corporation) at 8000 rpm for 10 minutes for emulsification. Thus, a milk-like emulsified flavor composition in the form of an O/W emulsion was prepared, whose absorbance at a wavelength 680 nm in 1/2000 dilution with ion-exchanged water was 0.2 Abs. One prepared by emulsifying the reference product 1 was referred to as a milk-like emulsified flavor composition of a comparative product 5, one prepared by emulsifying the reference product 2 was referred to as that of an invention product 27, one prepared by emulsifying the reference product 3 was referred to as that of an invention product 28, one prepared by emulsifying the reference product 4 was referred to as that of an invention product 29, one prepared by emulsifying the reference product 5 was referred to as that of an invention product 30, one prepared by emulsifying the reference product 6 was referred to as that of an invention product 31, and one prepared by emulsifying the reference product 7 was referred to as that of an invention product 32.

Example 26: Addition of Milk-Like Emulsified Flavor Composition to Lacto-Ice

According to the formulation of the following Table 11, lacto-ice was prepared, and 0.01% of the milk-like compounded flavor composition of the invention products 27 to 32 or the comparative product 5 was added thereto. For preparing lacto-ice, all the materials were dissolved by heating and emulsified with a homogenizer at 150 kg/cm², and then aged overnight at 10° C. This was frozen with a freezer, and then hardened up at −40° C. for 1 hour to give lacto-ice.

TABLE 11

| Sweetened condensed milk | 4 | Part by mass |
|---|---|---|
| Skim milk | 7 | " |
| Vegetable oil and fat | 9 | " |
| Sugar | 10 | " |
| Egg yolk | 12.5 | " |
| Stabilizer | 0.3 | " |
| Emulsifier | 0.4 | " |
| Vanilla flavor | 0.1 | " |
| Water | balance | " |
| Total | 100 | " |

Well-trained 5 panelists tasted the lacto-ice added with the milk-like emulsified flavor composition of the invention products 27 to 32 or the comparative product 5, and the non-added lacto-ice for organoleptic evaluation. As a result, all the five panelists first concluded that the lacto-ice added with the comparative product 5 provided better milk-like flavor than the lacto-ice not added with the flavor. Further, all the five panelists concluded that the lacto-ice added with any of the invention products 27 to 32 provided better milk-like flavor than the lacto-ice added with the comparative product 5 and that, regarding taste, the former provided enhanced umami, sweetness and milk richness and were all extremely delicious and good.

Example 27: Milk-Like Powdery Flavor Composition

As an aqueous phase, 70 g of gum arabic and 20 g of trehalose were dissolved in 150 g of water, and sterilized by heating at 85 to 90° C. for 15 minutes, and then cooled down to 40° C. As an oily phase, 10 g of the reference product 2 was added thereto and mixed, and then emulsified with a TK-homogenizer to produce an O/W emulsified composition. The emulsified composition was spray-dried, using a mobile minor spray drier by Niro, at an inlet temperature of 140° C. and an outlet temperature of 75° C. to produce 95 g of a milk-like powdery flavor composition (invention product 33: 2-(4-benzyloxybutyl)pyridine concentration 0.1% by mass).

Example 28: Addition to Aqueous Solution of Skim Milk

Skim milk, and a mixture of 99 parts by mass of skim milk and 1 part by mass of the invention product 33 were prepared by thorough mixing. 10 parts by mass of the skim milk or the mixture of skim milk and the invention product 33 was mixed with 90 parts by mass of water to prepare a mixture solution (aqueous solution of skim milk). Well-trained 5 panelists tasted these for organoleptic evaluation. As a result, all the five panelists concluded that the aqueous solution of skim milk added with the invention product 33 was better than the non-added aqueous solution of skim milk in that the former provided stronger milky flavor, stronger umami and sweetness, and stronger milk richness, namely, the former had an extremely good milky taste.

Example 29: Pineapple-Like Emulsified Flavor Composition

According to the formulation of the following Table 12, a pineapple-like compounded flavor composition was prepared (reference products 8 to 13).

TABLE 12

| | Formulation of Pineapple-like Compounded Flavor (part by mass) | | | | | |
|---|---|---|---|---|---|---|
| | Reference Product 8 | Reference Product 9 | Reference Product 10 | Reference Product 11 | Reference Product 12 | Reference Product 13 |
| Ethyl acetate | 12 | 12 | 12 | 12 | 12 | 12 |
| Ethyl butyrate | 10 | 10 | 10 | 10 | 10 | 10 |
| Isoamyl acetate | 4 | 4 | 4 | 4 | 4 | 4 |
| Isoamyl valerate | 2.2 | 2.2 | 2.2 | 2.2 | 2.2 | 2.2 |
| Isobutyric acid | 2.8 | 2.8 | 2.8 | 2.8 | 2.8 | 2.8 |
| Isovaleric acid | 1.2 | 1.2 | 1.2 | 1.2 | 1.2 | 1.2 |
| Allyl caproate | 1.4 | 1.4 | 1.4 | 1.4 | 1.4 | 1.4 |
| Ethyl caproate | 0.8 | 0.8 | 0.8 | 0.8 | 0.8 | 0.8 |
| Ethyl caprylate | 0.6 | 0.6 | 0.6 | 0.6 | 0.6 | 0.6 |
| Ethyl caprate | 0.8 | 0.8 | 0.8 | 0.8 | 0.8 | 0.8 |

TABLE 12-continued

Formulation of Pineapple-like Compounded Flavor (part by mass)

|  | Reference Product 8 | Reference Product 9 | Reference Product 10 | Reference Product 11 | Reference Product 12 | Reference Product 13 |
|---|---|---|---|---|---|---|
| Isoamyl alcohol | 1.4 | 1.4 | 1.4 | 1.4 | 1.4 | 1.4 |
| Diethyl malonate | 1.2 | 1.2 | 1.2 | 1.2 | 1.2 | 1.2 |
| Citral | 0.6 | 0.6 | 0.6 | 0.6 | 0.6 | 0.6 |
| Linalool | 0.2 | 0.2 | 0.2 | 0.2 | 0.2 | 0.2 |
| Maltol | 0.8 | 0.8 | 0.8 | 0.8 | 0.8 | 0.8 |
| Invention product 1 | 0.2 | — | — | — | — | — |
| Invention product 2 | — | 0.2 | — | — | — | — |
| Invention product 3 | — | — | 0.2 | — | — | — |
| Invention product 4 | — | — | — | 0.2 | — | — |
| Invention product 5 | — | — | — | — | 0.2 | — |
| Invention product 6 | — | — | — | — | — | 0.2 |
| Middle chain fatty acid triglyceride | balance | balance | balance | balance | balance | balance |
| total | 1000 | 1000 | 1000 | 1000 | 1000 | 1000 |

As an oily phase, 100 g of the pineapple-like compounded flavor composition of Table 12 (reference products 8 to 13), and as an aqueous phase, 312.5 g of glycerin and 22.5 g of decaglycerin monooleate dissolved in 65 g of ion-exchanged water were prepared, and the two liquids were mixed by stirring with a TK-homogenizer (manufactured by Primix Corporation) at 8000 rpm for 10 minutes for emulsification. Thus, a pineapple-like emulsified flavor composition in the form of an O/W emulsion was prepared, whose absorbance at a wavelength 680 nm in 1/2000 dilution with ion-exchanged water was 0.2 Abs. One prepared by emulsifying the reference product 8 was referred to as a pineapple-like emulsified flavor composition of an invention product 34, one prepared by emulsifying the reference product 9 was referred to as that of an invention product 35, one prepared by emulsifying the reference product 10 was referred to as that of an invention product 36, one prepared by emulsifying the reference product 11 was referred to as that of an invention product 37, one prepared by emulsifying the reference product 12 was referred to as that of an invention product 38, and one prepared by emulsifying the reference product 13 was referred to as that of an invention product 39.

Example 30: Addition of Pineapple-Like Compounded Flavor Composition to Sherbet

According to the formulation of the following Table 13, sherbet was prepared, and 0.2% of the pineapple-like emulsified flavor composition of the invention products 34 to 39 was added thereto.

TABLE 13

| Sugar | 10 | part by mass |
|---|---|---|
| Starch syrup (75%) | 6 | " |
| Fructose sucrose liquid sugar (75%) | 5 | " |
| Citric acid (crystal) | 0.1 | " |
| 20% pineapple juice | 10 | " |
| Water | balance | " |
| Total | 100 | " |

Five panelists ate these sherbet products for organoleptic evaluation. As a result, all the five panelists concluded that the sherbet added with the invention products 34 to 39 had fresher and better pineapple characteristics of natural impression than the non-added sherbet, saying that, regarding the taste thereof, the former realized better umami and sweetness than the latter.

Example 101: Preparation of 2-(3-benzyloxypropyl)pyridine

An aqueous 25 wt % sodium hydroxide solution (44.24 g, 277 mmol), 2-pyridinepropanol (5.00 g, 36.4 mmol), benzyl chloride (5.53 g, 43.7 mmol) and tetra-n-butylammonium bromide (0.59 g, 1.8 mmol) were put into a 200-mL flask, and stirred at 45° C. for 3 hours. The reaction liquid was cooled down to room temperature, extracted with 50 mL of hexane added thereto, and the organic layer was separated. 2 Mol/l hydrochloric acid (50 mL) was added to the organic layer, and 2-(3-benzyloxypropyl)pyridine was extracted out in the aqueous layer as a hydrochloride thereof. Subsequently, an aqueous 25 wt. % sodium hydroxide solution was added to the aqueous layer to have a pH of 9 for neutralization of the hydrochloride, and then extracted with ethyl acetate (50 mL). The organic layer was washed with 20% saline water (50 mL), and dried with anhydrous magnesium sulfate added thereto. The solvent was evaporated away under reduced pressure using a rotary evaporator to give a concentrated product (6.09 g). This was purified through distillation under reduced pressure to give 2-(3-benzyloxypropyl)pyridine (yield: 4.34 g, 52.5%, purity: 99.6%) (invention product 101).

Physical Data of 2-(3-benzyloxypropyl)pyridine

Boiling point: 152 to 155° C./0.13 kPa
1H NMR (CDCl$_3$, 400 MHz) δ 2.07 (tt, 2H, J=7.8, 6.0 Hz), 2.89 (t, 2H, J=7.8 Hz), 3.53 (t, 2H, J=6.0 Hz), 4.51 (s, 2H), 7.10 (ddd, 1H, J=7.6, 5.2, 1.2 Hz), 7.14 (d, 1H, J=7.6 Hz), 7.26-7.35 (m, 5H), 7.57 (dt, 1H, J=2.0, 7.6 Hz), 8.52 (dd, 1H, J=4.8, 0.8 Hz).
$^{13}$C NMR (CDCl$_3$, 100 MHz) δ 29.65, 34.87, 69.56, 72.81, 120.95, 122.83, 127.46, 127.59 (2C), 128.31 (2C), 136.22, 138.54, 149.24, 161.68.
MS (EI, 70 eV) m/z 65 (8), 78 (5), 91 (30), 92 (12), 93 (100), 94 (8), 106 (13), 118 (6), 120 (15), 121 (10), 136 (86), 137 (8).

Example 102: Evaluation of Flavor of 2-(3-benzyloxypropyl)pyridine

A 0.1% ethanol solution of the invention product 101 (2-(3-benzyloxypropyl)pyridine) prepared in Example 101 was prepared as an evaluation solution. The evaluation solution was prepared in a sample bottle. Regarding the flavor of the sample smelling from the bottle mouth and the flavor of a flavor paper prepared by infiltrating the evaluation solution into a paper, well-trained 5 panelists tested the solution for flavor evaluation. A typical evaluation of the product is as follows.

Flavor evaluation (average evaluation of 5 panelists): somewhat herbal, green and nutty flavor of natural impression.

Example 103: Pineapple-Like Compounded Flavor Composition

According to the formulation of the following Table 14, a pineapple-like compounded flavor composition was prepared to be a comparative product 101.

TABLE 14

| Ethyl acetate | 12 | part by mass |
| Ethyl butyrate | 10 | " |
| Isoamyl acetate | 4 | " |
| Isoamyl valerate | 2.2 | " |
| Isobutyric acid | 2.8 | " |
| Isovaleric acid | 1.2 | " |
| Allyl caproate | 1.4 | " |
| Ethyl caproate | 0.8 | " |
| Ethyl caprylate | 0.6 | " |
| Ethyl caprate | 0.8 | " |
| Isoamyl alcohol | 1.4 | " |
| Diethyl malonate | 1.2 | " |
| Citral | 0.6 | " |
| Linalool | 0.2 | " |
| Maltol | 0.8 | " |
| Propylene glycol | 500 | " |
| 95% ethanol | 460 | " |
| Total | 1000 | |

0.2 g (0.02% by mass) of the invention product 101 (2-(3-benzyloxypropyl)pyridine) was mixed in 999.8 g of the above-mentioned, pineapple-like compounded flavor composition (comparative product 101) to prepare a novel pineapple-like compounded flavor composition (invention product 102). Well-trained five panelists compared the novel pineapple-like compounded flavor composition and the above-mentioned pineapple compounded flavor composition not added with the compound of the invention product 101. For flavor evaluation, 10 ml of the flavor composition was prepared in a sample bottle (30 ml). The well-trained five panelists evaluated the flavor smelling from the bottle mouth and the flavor of the flavor paper prepared by infiltrating the flavor composition into a paper. As a result, all of the five expert panelists concluded that the novel compounded flavor composition (invention product 102) added with the compound had fresher and better pineapple characteristics of natural impression than the comparative product 101 and was remarkably more excellent than the latter in point of the flavor durability.

Example 104: Incorporation of Pineapple-Like Compounded Flavor Composition in Sherbet The pineapple-like compounded flavor composition (comparative product 101 or invention product 102) obtained in Example 103 was added to sherbet having the following formulation to prepare sherbet according to an ordinary method, and well-trained 5 panelists ate it for organoleptic evaluation.

Sherbet Compounding Formulation (Part by Mass)
Sugar: 10, starch syrup (75%): 6, fructose sucrose liquid sugar syrup (75%): 5, citric acid (crystal): 0.1, 20% pineapple juice: 10, invention product 102 (or comparative product 101): 0.2, water to make a total amount of 100.

Five panelists ate these sherbet products for organoleptic evaluation. As a result, all the five panelists concluded that the sherbet added with the invention product 102 had fresher and better pineapple characteristics of natural impression than the sherbet added with comparative product 101, and evaluated that, regarding the taste thereof, the former realized better umami and sweetness than the latter.

Example 105: Lilac-Type Compounded Flavor Composition

According to the formulation of the following Table 15, a lilac-type compounded flavor composition was prepared (comparative product 102).

TABLE 15

| Phenylethyl acetate | 4 | part by mass |
| Cinnamic alcohol | 16 | " |
| Terpineol | 52 | " |
| Cyclamen aldehyde | 4 | " |
| Heliotropine | 20 | " |
| Cinnamyl acetate | 4 | " |
| Carnation absolute | 8 | " |
| Linalool | 12 | " |
| Indole | 0.8 | " |
| Styrax resinoid | 12 | " |
| Ylang-ylang | 4 | " |
| Hydroxycitronellal | 116 | " |
| Benzyl acetate | 8 | " |
| Anisaldehyde | 8 | " |
| Absolute jasmine | 8 | " |
| Phenylethyl alcohol | 111.2 | " |
| Anise alcohol | 12 | " |
| 1,3-butylene glycol | 600 | " |
| Total | 1000 | |

0.2 g (0.2% by mass) of 2-(3-benzyloxypropyl)pyridine was mixed in 99.8 g of the above-mentioned lilac-type flavor composition (comparative product 102) to prepare a novel lilac-type compounded flavor composition (invention product 103). Five panelists compared the novel compounded flavor composition with the comparative product 102. As a result, all the panelists concluded that the novel compounded flavor composition (invention product 103) added with the compound had fresher lilac characteristics of natural impression than the comparative product 102 and was remarkably more excellent than the latter in point of the flavor durability.

Example 106: Incorporation of Lilac-Type Compounded Flavor Composition in Shampoo The lilac-type compounded flavor composition (comparative product 102 or invention product 103) obtained in Example 105 was added to shampoo having the following formulation to prepare shampoo according to an ordinary method, and well-trained 5 panelists tried it in shampooing for organoleptic evaluation.

Shampoo Formulation (Part by Mass)
Sodium polyoxyethylene laurylsulfate: 20, coconut oil fatty acid diethanolamide: 5, glycerin: 4, invention product 103 (or comparative product 102); 0.2, water to make a total amount of 100.

Five panelists tested these shampoo products for organoleptic evaluation. As a result, all the five panelists concluded that the shampoo added with the invention product 103 had fresher and better lilac characteristics of natural impression than the shampoo added with the comparative product 102.

Example 107: Confirmation of Umami

A solution was prepared by dissolving 2-(3-benzyloxypropyl)pyridine (invention product 101) in water to have a concentration shown in Table 15. As a comparative product, a solution was prepared by dissolving 2-(2-benzyloxyethyl)pyridine (comparative product 1 prepared in Comparative Example 1) to have the same concentration. Well-trained 5 panelists tasted the solutions and non-added water for organoleptic evaluation of taste and flavor.

Average evaluation results of the five panelists are shown in the following Table 16.

the concentration fell within a range of 0.1 ppm to 2000 ppm by mass, and in particular, provided good umami when the concentration was 1 ppm to 200 ppm or so.

Specifically, it is recognized that the umami imparting effect of 2-(3-benzyloxypropyl)pyridine is stronger by 10 times or so than 2-(2-benzyloxyethyl)pyridine, and the concentration of 2-(3-benzyloxypropyl)pyridine to provide the same umami intensity was about 1/10 that of 2-(2-benzyloxyethyl)pyridine.

Example 108: Confirmation of Umami Imparting and Saltiness Enhancing Effect

An aqueous 0.3 mass % sodium chloride solution (control), and solutions of 2-(3-benzyloxypropyl)pyridine dis-

TABLE 16

| | Organoleptic Evaluation | | | |
|---|---|---|---|---|
| | 2-(3-benzyloxypropyl)pyridine (invention product 101) | | 2-(2-benzyloxyethyl)pyridine (comparative product 1) | |
| Addition Concentration | Taste | Flavor | Taste | Flavor |
| 2 ppb | No difference from water. | Nothing at all. | No difference from water. | Nothing at all. |
| 10 ppb | Slightly umami | Extremely slightly somewhat herbal, green and nutty flavor of natural impression. | No difference from water. | Nothing at all. |
| 0.1 ppm | Weakly umami. | Slightly somewhat herbal, green and nutty flavor of natural impression. | Slightly umami. | Extremely slightly earthy flavor associated with fresh grass roots. |
| 1 ppm | Umami. The quality of umami is natural and appetizing. | Somewhat herbal, green and nutty flavor of natural impression. | Weakly umami. | Slightly earthy flavor associated with fresh grass roots. |
| 20 ppm | Strongly umami. | Somewhat herbal, green and nutty flavor of natural impression. | Umami. The quality of umami is natural and appetizing. | Earthy flavor associated with fresh grass roots. |
| 200 ppm | Extremely strong umami, but associated with bitterness. | Somewhat herbal, green and nutty flavor of natural impression. | Strongly umami. | Earthy flavor associated with fresh grass roots. |
| 500 ppm | Strong umami and bitterness, and the balance of the two is not good. | Too strong flavor and poor balance. | Extremely strong umami, but associated with bitterness. | Extremely strong earthy flavor associated with fresh grass roots. |
| 2000 ppm | Strong umami and bitterness, and the balance of the two is not good. | Too strong flavor and poor balance. | Strong umami and bitterness, and the balance of the two is not good. | Too strong flavor and poor balance. |

As shown in Table 16, the aqueous solution prepared by dissolving 2-(3-benzyloxypropyl)pyridine (invention product 101) alone in water was tasty, and the taste thereof was umami. Regarding the concentration, it is known that the compound gave umami in an amount falling within a range of, by mass, 0.01 ppm to 200 ppm, and gave especially good umami within a range of 0.1 ppm to 20 ppm or so.

On the other hand, the aqueous solution prepared by dissolving 2-(2-benzyloxyethyl)pyridine (comparative product 1) alone in water was also tasty and the taste thereof was umami. It is known that the solution provided umami when solved in a 0.3 mass % sodium chloride solution to have the concentration shown in Table 17 were prepared. As comparative products, an aqueous 0.3 mass % sodium chloride solution (control), and a solution of a comparative product, 2-(2-benzyloxyethyl)pyridine dissolved in a 0.3 mass % sodium chloride solution to have the same concentration were prepared. Well-trained 5 panelists tasted the solutions for organoleptic evaluation of umami impartment and saltiness enhancement. Average evaluation results are shown in the following Table 17.

TABLE 17

| | Organoleptic Evaluation | |
|---|---|---|
| Addition Concentration | 2-(3-benzyloxypropyl)pyridine (invention product 101) | 2-(2-benzyloxyethyl)pyridine (comparative product 1) |
| 0.05 ppb | No difference from control (aqueous 0.3 mass % sodium chloride solution). | No difference from control (aqueous 0.3 mass % sodium chloride solution). |

TABLE 17-continued

| | Organoleptic Evaluation | |
|---|---|---|
| Addition Concentration | 2-(3-benzyloxypropyl)pyridine (invention product 101) | 2-(2-benzyloxyethyl)pyridine (comparative product 1) |
| 0.1 ppb | Extremely slightly umami and saltiness, as compared with control. | No difference from control (aqueous 0.4 mass % sodium chloride solution). |
| 1 ppb | Slightly umami as compared with control. | Extremely slightly umami as compared with control. |
| 10 ppb | Umami and saltiness as compared with control. | Slightly umami as compared with control. |
| 0.1 ppm | Distinctly umami and saltiness as compared with control. The quality of umami and saltiness is good, natural and appetizing. | Umami as compared with control. |
| 0.5 ppm | Strongly umami and saltiness as compared with control. The quality of umami and saltiness is good, natural and appetizing. | Distinctly umami as compared with control. The quality of umami is good, natural and appetizing. |
| 2 ppm | Extremely strongly umami and saltiness as compared with control, but somewhat too much. | Strongly umami as compared with control. The quality of umami is good, natural and appetizing. |
| 10 ppm | Too much umami and saltiness as compared with control, additionally somewhat bitterness. | Extremely strongly umami as compared with control, but somewhat too much. |
| 50 ppm | Too much umami and saltiness as compared with control, additionally somewhat bitterness. | Too much umami as compared with control, additionally somewhat bitterness. |

As shown in Table 17, the aqueous solution prepared by dissolving 2-(3-benzyloxypropyl)pyridine (invention product 101) in an aqueous 0.3 mass % sodium chloride solution had umami and salty taste, and the solution provided umami at a lower concentration by about 1/10 than that of the solution prepared by dissolving the product in water. Accordingly, the concentration of 2-(3-benzyloxypropyl) pyridine capable of realizing umami impartation and saltiness enhancement when combined with edible salt is considered to be within a range of 1 ppb to 200 ppm by mass, preferably 0.01 ppm to 50 ppm, more preferably 0.1 ppm to 10 ppm. In addition, it is recognized that the umami imparting effect of 2-(3-benzyloxypropyl)pyridine is higher by about 10 times than that of 2-(2-benzyloxyethyl)pyridine (comparative product 1), and the concentration of 2-(3-benzyloxypropyl)pyridine to realize the same degree of umami intensity is about 1/10 that of 2-(2-benzyloxyethyl) pyridine.

Example 109: Confirmation of Umami and Saltiness Enhancement

Well-trained 5 panelists tasted an aqueous solution of 0.3 mass % edible salt and 0.03 mass % sodium glutamate (MSG), and an aqueous solution prepared by adding to the aqueous solution, 10 ppb of 2-(3-benzyloxypropyl)pyridine (invention product 101), for organoleptic evaluation in point of umami and saltiness enhancement. As a result, all the five panelists concluded that the aqueous solution added with 10 ppb of 2-(3-benzyloxypropyl)pyridine gave stronger umami and saltiness.

Example 110: Confirmation of Umami Enhancing Effect

Well-trained 5 panelists tasted an aqueous solution of 0.3 mass % edible salt and 0.05 mass % sodium glutamate (MSG), and an aqueous solution of 0.3 mass % edible salt and 10 ppb of 2-(3-benzyloxypropyl)pyridine (invention product 101), for organoleptic evaluation of umami. As a result, all the five panelists concluded that the two had umami of almost the same level.

Example 111: Confirmation of Umami Enhancing Effect

Well-trained 5 panelists tasted an aqueous solution of 0.1 mass % sodium inosinate (5'-IMP.2Na), and an aqueous solution prepared by adding thereto 10 ppb of 2-(3-benzyloxypropyl)pyridine (invention product 101), for organoleptic evaluation in point of umami. As a result, all the five panelists concluded that the aqueous solution added with 10 ppb of 2-(3-benzyloxypropyl)pyridine gave stronger umami.

Example 112: Confirmation of Sweetness Enhancing Effect

Well-trained 5 panelists tasted an aqueous 3 mass % sucrose solution, and an aqueous solution prepared by adding thereto 5 ppb of 2-(3-benzyloxypropyl)pyridine (invention product 101), for organoleptic evaluation in point of sweetness. As a result, all the five panelists concluded that the aqueous solution added with 5 ppb of 2-(3-benzyloxypropyl) pyridine gave stronger sweetness.

Example 113: Addition to Soup Broth for Udon Noodle 0.05 ppm of 2-(3-benzyloxypropyl)pyridine (invention product 101) was added to commercially-available soup broth for udon noodle (tripe strength). 200 ml of hot water was added to 100 ml of each of the added soup broth and the non-added soup broth, and well-trained 5 panelists tasted them for organoleptic evaluation in point of umami. As a result, all the five panelists concluded that the soup broth added with 0.05 ppm of 2-(3-benzyloxypropyl)pyridine provided stronger umami, saltiness and sweetness.

Example 114: Katsuobushi-Like Compounded Flavor Composition (a Type that Imparts Umami in Addition to Flavor)

According to the formulation of the following Table 18, a katsuobushi-like compounded flavor composition was prepared.

TABLE 18

| | | |
|---|---|---|
| 1,2,3-trimethoxy-5-methylbenzene | 40 | part by mass |
| Isosafrole | 2 | " |
| 2-penten-1-ol | 8 | " |
| Trans-2-pentenal | 1 | " |
| Cyclotene | 10 | " |
| Diacetyl | 5 | " |
| 2-methylfuran | 20 | " |
| Acetic acid | 3 | " |
| γ-butyrolactone | 1 | " |
| (E,Z,Z)-2,4,7-tridecatrienal | 0.00005 | " |
| 4,7-tridecadienal | 0.00005 | " |
| Trimethylamine | 0.00001 | " |
| 2-methylfuran-3-thiol | 0.00005 | " |
| 2-(3-benzyloxypropyl)pyridine | 1 | " |
| 95% ethanol | 100 | " |
| Propylene glycol | balance | " |
| Total | 1000 | |

Example 115: Addition of Katsuobushi-Like Compounded Flavor Composition to Mentsuyu According to the formulation of the following Table 19, mentsuyu was prepared, and 0.02% of the katsuobushi-like compounded flavor composition prepared in Example 114 was added thereto.

TABLE 19

| | | |
|---|---|---|
| Soy sauce | 500 | Part by mass |
| Mirin | 200 | " |
| Sugar | 100 | " |
| Yeast extract | 6 | " |
| Water | 194 | " |
| Total | 1000 | |

Well-trained 5 panelists tasted the mentsuyu not added with the katsuobushi-like compounded flavor composition and the katsuobushi-like compounded flavor composition-added mentsuyu for organoleptic evaluation. As a result, all the five panelists concluded that the mentsuyu added with the katsuobushi-like compounded flavor composition of the present invention was good as given a katsuobushi-like flavor, additionally saying that the taste thereof covered enhanced umami, saltiness and sweetness, that is, the mentsuyu was extremely delicious and good.

Example 116: Milk-Like Compounded Flavor Composition (a Type that Imparts Richness in Addition to Flavor)

According to the formulation of the following Table 20, a milk-like compounded flavor composition (comparative product 104) was prepared.

TABLE 20

| | | |
|---|---|---|
| Vanillin | 25.0 | part by mass |
| Ethylvanillin | 35.0 | " |
| Maple lactone | 2.5 | " |
| Ethylmaltol | 3.5 | " |
| γ-undecalactone | 2.0 | " |
| γ-nonalactone | 10.0 | " |
| δ-decalactone | 2.5 | " |
| Acetylmethylcarbinol | 3.0 | " |
| Diacetyl | 7.0 | " |
| Butyric acid | 5.0 | " |
| Propylene glycol | 904.5 | " |
| Total | 1000.0 | " |

One mg (10 ppm) of 2-(3-benzyloxypropyl)pyridine was mixed in 100 g of the milk-like compounded flavor composition (comparative product 104) to prepare a milk-like compounded flavor composition of an invention product 104.

Example 117: Addition to Aqueous Solution of Skim Milk

A mixed solution (aqueous solution of skin milk) of 10 parts by mass of skim milk and 90 parts by mass of water was prepared, and 0.1% of the milk-like compounded flavor composition prepared in Example 116 was added thereto. Well-trained 5 panelists tasted the aqueous solution of skim milk not added with the milk-like compounded flavor composition, the aqueous solution of skim milk added with 0.1% by mass of any of the comparative product 104 and the aqueous solution of skim milk added with 0.1% by mass of any of the invention product 104 for organoleptic evaluation. As a result, all the five panelists concluded that the aqueous solution of skim milk added with the comparative product 104 was better-tasting than the non-added aqueous solution of skim milk as given enriched milk flavor, further saying that the aqueous solution of skim milk added with the invention product 104 was extremely better than the aqueous solution of skim milk added with the comparative product 104 as given stronger umami and sweetness and further given stronger milk richness, that is, the former had an extremely good milk-like taste.

Reference Example 201: Confirmation of Umami

The invention product 101 and the comparative product 1 were individually diluted with ethanol to have a proper concentration, and then further diluted with water to prepare an aqueous solution of 2-(3-benzyloxypropyl)pyridine (invention product 101 produced in Example 101) and that of 2-(2-benzyloxyethyl)pyridine (comparative product 1 synthesized in Comparative Example 1) each having a concentration shown in the following Table 21. Well-trained panelists tasted the solution having a different concentration and non-added water for organoleptic evaluation in point of taste and flavor.

Average evaluation results of the five panelists are shown in Table 21.

TABLE 21

| Addition Concentration | 2-(3-benzyloxypropyl)pyridine (invention product 101) | | 2-(2-benzyloxyethyl)pyridine (comparative product 1) | |
|---|---|---|---|---|
| | Taste | Flavor | Taste | Flavor |
| 2 ppb | No difference from water. | Nothing at all. | No difference from water. | Nothing at all. |
| 10 ppb | Slightly umami. | Extremely slightly somewhat herbal, green and nutty flavor of natural impression. | No difference from water. | Nothing at all. |
| 0.1 ppm | Weakly umami. | Slightly somewhat herbal, green and nutty flavor of natural impression. | Slightly umami. | Extremely slightly earthy flavor associated with fresh grass roots. |
| 1 ppm | Umami. The quality of umami is natural and appetizing. | Somewhat herbal, green and nutty flavor of natural impression. | Weakly umami. | Slightly earthy flavor associated with fresh grass roots. |
| 20 ppm | Strongly umami. | Somewhat herbal, green and nutty flavor of natural impression. | Umami. The quality of umami is natural and appetizing. | Earthy flavor associated with fresh grass roots. |
| 200 ppm | Extremely strong umami, but associated with bitterness. | Somewhat herbal, green and nutty flavor of natural impression. | Strongly umami. | Earthy flavor associated with fresh grass roots. |

As shown in Table 21, the aqueous solution of 2-(3-benzyloxypropyl)pyridine (invention product 101) was tasty, and the taste thereof was umami. Regarding the concentration, it is known that the compound gave umami in an amount falling within a range of, by mass, 0.01 ppm to 200 ppm, and gave especially good umami within a range of 0.1 ppm to 20 ppm or so.

On the other hand, the aqueous solution of 2-(2-benzyloxyethyl)pyridine (comparative product 1) was also tasty and the taste thereof was umami. It is known that the solution provided umami when the concentration fell within a range of 0.1 ppm to 2000 ppm by mass, and in particular, provided good umami when the concentration was 1 ppm to 200 ppm or so.

Specifically, it is recognized that the umami imparting effect of 2-(3-benzyloxypropyl)pyridine is stronger by 10 times or so than 2-(2-benzyloxyethyl)pyridine, and the concentration of 2-(3-benzyloxypropyl)pyridine to provide the same umami intensity was about 1/10 that of 2-(2-benzyloxyethyl)pyridine.

Example 201: Preparation of Emulsified Composition Containing 2-(3-benzyloxypropyl)pyridine As an oily phase, 2-(3-benzyloxypropyl)pyridine (1.0 g), SAIB (sucrose acetate isobutyrate) (9.0 g) and MCT (middle-chain fatty acid triglyceride) (9.0 g) were mixed and dissolved, and as an aqueous phase, 66 g of glycerin, 11 g of ion-exchanged water and decaglycerin monooleate (4.0 g) were mixed and dissolved, and the two liquids were mixed by stirring with a TK-homogenizer (manufactured by Primix Corporation) at 8000 rpm for 10 minutes for emulsification. Thus, an O/W emulsion was prepared, whose absorbance at a wavelength 680 nm in 1/2000 dilution with ion-exchanged water was 0.2 Abs (invention product 201: 2-(3-benzyloxypropyl)pyridine concentration 1.0%).

Reference Example 202: Ethanol Solution of 2-(3-benzyloxypropyl)pyridine 2-(3-Benzyloxypropyl)pyridine (1.0 g) was dissolved in 99.0 g of 99.5% ethanol to prepare a solution thereof (reference product 202: 2-(3-benzyloxypropyl)pyridine concentration 1.0%).

Example 202: Confirmation of Umami

The invention product 201 and the reference product 202 was individually dissolved in water to prepare a 2-(3-benzyloxypropyl)pyridine solution having a concentration shown in the following Table 22. Well-trained 5 panelists tasted the solutions for organoleptic evaluation in point of taste and flavor Average evaluation results of the five panelists are shown in Table 22.

TABLE 22

| 2-(3-Benzyl-oxypropyl)pyridine | Emulsified Product (invention product 201) | | Ethanol-Diluted Product (reference product 202) | |
|---|---|---|---|---|
| Concentration | Taste | Flavor | Taste | Flavor |
| 2 ppb | No difference from water. | Nothing at all. | No difference from water. | Nothing at all. |
| 10 ppb | Slightly umami. As compared with ethanol-diluted product, mild but persistent. | Extremely slightly somewhat herbal, green and nutty flavor of natural impression. | Slightly umami. | Extremely slightly somewhat herbal, green and nutty flavor of natural impression. |

TABLE 22-continued

| | Organoleptic Evaluation | | | |
|---|---|---|---|---|
| 2-(3-Benzyl-oxypropyl)pyridine | Emulsified Product (invention product 201) | | Ethanol-Diluted Product (reference product 202) | |
| Concentration | Taste | Flavor | Taste | Flavor |
| 0.1 ppm | Weakly umami. As compared with ethanol-diluted product, mild but persistent. | Slightly somewhat herbal, green and nutty flavor of natural impression. | Weakly umami. | Slightly somewhat herbal, green and nutty flavor of natural impression. |
| 1 ppm | Umami. The quality of umami is natural and appetizing. As compared with ethanol-diluted product, mild but persistent. | Somewhat herbal, green and nutty flavor of natural impression. | Umami. The quality of umami is natural and appetizing. | Somewhat herbal, green and nutty flavor of natural impression. |
| 20 ppm | Strongly umami. As compared with ethanol-diluted product, mild but persistent. | Somewhat herbal, green and nutty flavor of natural impression. | Strongly umami. | Somewhat herbal, green and nutty flavor of natural impression. |
| 200 ppm | Extremely strong umami, but associated with bitterness. As compared with ethanol-diluted product, mild but persistent. | Somewhat herbal, green and nutty flavor of natural impression. | Strongly umami. | Earthy flavor associated with fresh green roots. |

As shown in Table 22, both the aqueous dilution of the ethanol-diluted 2-(3-benzyloxypropyl)pyridine (reference product 202) and the aqueous dilution of the emulsified product (invention product 201) had umami, but the result was that the emulsified product was milder and more persistent than the ethanol-diluted product having the same 2-(3-benzyloxypropyl)pyridine concentration.

Example 203: Confirmation of Umami Imparting and Saltiness Enhancing Effect

An aqueous 0.3 mass % sodium chloride solution (control), and solutions of the invention product 201 or the reference product 202 dissolved in a 0. mass % sodium chloride solution to have the concentration as 2-(3-benzyloxypropyl)pyridine therein shown in the following Table 23 were prepared. Well-trained 5 panelists tasted the solutions for organoleptic evaluation of umami impartment and saltiness enhancement. Average evaluation results are shown in Table 23.

TABLE 23

| 2-(3-Benzyl-oxypropyl)pyridine Addition | Organoleptic Evaluation | |
|---|---|---|
| Concentration | Emulsified Product (invention product 201) | Ethanol Dilution (reference product 202) |
| 0.05 ppb | No difference from control (aqueous 0.3 mass % sodium chloride solution). | No difference from control (aqueous 0.3 mass % sodium chloride solution). |
| 0.1 ppb | Extremely slightly umami and saltiness, as compared with control. | Extremely slightly umami and saltiness, as compared with control. |
| 1 ppb | Slightly umami as compared with control. | Slightly umami as compared with control. |
| 10 ppb | Umami and saltiness as compared with control. Milder and more persistent than ethanol dilution. | Umami and saltiness as compared with control. |
| 0.1 ppm | Distinctly umami and saltiness as compared with control. The quality of umami and saltiness is good, natural and appetizing. Milder and more persistent than ethanol dilution having the same concentration | Distinctly umami and saltiness as compared with control. The quality of umami and saltiness is good, natural and appetizing. |
| 0.5 ppm | Strongly umami and saltiness as compared with control. The quality of umami and saltiness is good, natural and appetizing. Milder and more persistent than ethanol dilution having the same concentration | Strongly umami and saltiness as compared with control. The quality of umami and saltiness is good, natural and appetizing. |
| 2 ppm | Extremely strongly umami and saltiness as compared with control. Natural umami and | Extremely strongly umami and saltiness as compared with control, but somewhat too much. |

TABLE 23-continued

| 2-(3-Benzyl-oxypropyl)pyridine Addition | Organoleptic Evaluation | |
| --- | --- | --- |
| Concentration | Emulsified Product (invention product 201) | Ethanol Dilution (reference product 202) |
| | saltiness without too much taste like ethanol dilution. | |
| 10 ppm | Too much umami and saltiness as compared with control, additionally strong bitterness. Not too much like ethanol dilution having the same concentration. | Too much umami and saltiness as compared with control, additionally somewhat bitterness. |
| 50 ppm | Too much umami and saltiness as compared with control, additionally strong bitterness. Not too much like ethanol dilution having the same concentration. | Too much umami and saltiness as compared with control, additionally somewhat bitterness. |

As shown in Table 23, the aqueous solution prepared by dissolving 2-(3-benzyloxypropyl)pyridine in an aqueous 0.3 mass % sodium chloride solution had umami and salty taste, and the solution provided umami at a lower concentration by about 1/10 than that of the solution prepared by dissolving the product in water. Accordingly, the concentration of 2-(3-benzyloxypropyl)pyridine capable of realizing umami impartation and saltiness enhancement when combined with edible salt is considered to be within a range of 0.1 ppb to 50 ppm by mass, preferably 1 ppb to 10 ppm, more preferably 10 ppb to 2 ppm.

In addition, the emulsified product of 2-(3-benzyloxypropyl)pyridine gave milder and more persistent umami and saltiness than the ethanol dilution thereof. In particular, it is recognized that, when having a high concentration (0.5 ppm or more), too much umami of the emulsified product is reduced more as compared with the ethanol dilution, and the emulsified product realized milder and persistent umami.

Example 204: Confirmation of Umami and Saltiness Enhancement

Well-trained 5 panelists tasted an aqueous solution of 0.3 mass % edible salt and 0.03 mass % sodium glutamate (MSG), and an aqueous solution prepared by adding to the aqueous solution, 10 ppb, as 2-(3-benzyloxypropyl)pyridine therein, of the invention product 201 or the reference product 202, for organoleptic evaluation in point of umami and saltiness enhancement. As a result, all the five panelists concluded that the aqueous solution added with 10 ppb of 2-(3-benzyloxypropyl)pyridine gave stronger umami and saltiness, and that the aqueous solution added with the invention product 201 (emulsified product) had milder and more persistent umami and saltiness than that added with the reference product 202 (ethanol dilution).

Example 205: Confirmation of Umami Enhancing Effect

Well-trained 5 panelists tasted (1) an aqueous solution of 0.3 mass % edible salt and 0.05 mass % sodium glutamate (MSG), and (2) and an aqueous solution of 0.3 mass % edible salt and 10 ppb, as 2-(3-benzyloxypropyl)pyridine therein, of the invention product 201, for organoleptic evaluation in point of umami. As a result, all the five panelists concluded that both the two [(1) and (2)] had nearly the same level of umami.

Example 206: Confirmation of Umami Enhancing Effect

Well-trained 5 panelists tasted (1) 0.1 mass % sodium inosinate (5'-IMP.2Na) and (2) an aqueous solution of 0.1 mass % sodium inosinate and 5 ppb, as 2-(3-benzyloxypropyl)pyridine therein, of the invention product 201, for organoleptic evaluation in point of umami. As a result, all the five panelists concluded that (2) added with 5 ppb of 2-(3-benzyloxypropyl)pyridine had stronger umami.

Example 207: Confirmation of Sweetness Enhancing Effect

Well-trained 5 panelists tasted (1) an aqueous 3 mass % sucrose solution and (2) an aqueous solution prepared by adding 5 ppb, as 2-(3-benzyloxypropyl)pyridine therein, of the invention product 201 to the aqueous 3 mass % sucrose solution, for organoleptic evaluation in point of sweetness. As a result, all the five panelists concluded that (2) added with 5 ppb of 2-(3-benzyloxypropyl)pyridine had stronger sweetness.

Example 208: Addition to Soup Broth for Udon Noodle 0.05 ppm as 2-(3-benzyloxypropyl)pyridine therein of the invention product 201 was added to commercially-available soup broth for udon noodle (tripe strength). 200 ml of hot water was added to 100 ml of each of the added soup broth and the non-added soup broth, and well-trained 5 panelists tasted them for organoleptic evaluation in point of umami. As a result, all the five panelists concluded that the soup broth added with 0.05 ppm of 2-(3-benzyloxypropyl)pyridine provided stronger umami, saltiness and sweetness.

Example 209: Katsuobushi-Like Emulsified Flavor Composition

According to the formulation of the following Table 24, a katsuobushi-like compounded flavor composition (reference product 203) was prepared.

TABLE 24

| 1,2,3-trimethoxy-5-methylbenzene | 40 | part by mass |
| --- | --- | --- |
| Isosafrole | 2 | " |
| 2-penten-1-ol | 8 | " |
| Trans-2-pentenal | 1 | " |
| Cyclotene | 10 | " |
| Diacetyl | 5 | " |
| 2-methylfuran | 20 | " |
| Acetic acid | 3 | " |
| γ-butyrolactone | 1 | " |
| (E,Z,Z)-2,4,7-tridecatrienal | 0.00005 | " |
| 4,7-tridecadienal | 0.00005 | " |

TABLE 24-continued

| Trimethylamine | 0.00001 | " |
| 2-methylfuran-3-thiol | 0.00005 | " |
| 2-(3-benzyloxypropyl)pyridine | 1 | " |
| Middle chain fatty acid triglyceride | balance | " |
| Total | 100 | |

100 g of the katsuobushi-like compounded flavor composition of the above Table 24 (referenced product 203: 2-(3-benzyloxypropyl)pyridine concentration 1.0 mass %) as an oily phase, and a solution of 312.5 g of glycerin, and 22.5 g of decaglycerin monostearate dissolved in 65 g of ion-exchanged water as an aqueous phase were prepared. The two were mixed by stirring with a TK-homogenizer (manufactured by Primix Corporation) at 8000 rpm for 10 minutes for emulsification. Thus, a katsuobushi-like emulsified flavor composition in the form of an O/W emulsion was prepared, whose absorbance at a wavelength 680 nm in 1/2000 dilution with ion-exchanged water was 0.2 Abs (invention product 202: 2-(3-benzyloxypropyl)pyridine concentration 0.2% by mass).

Example 210: Addition of Katsuobushi-Like Emulsified Flavor Composition to Mentsuyu According to the formulation of the following Table 25, mentsuyu was prepared, and 0.01% of the katsuobushi-like emulsified flavor composition of the invention product 202 was added thereto (2-(3-benzyloxypropyl)pyridine concentration 0.2 ppm).

TABLE 25

| Soy sauce | 500 | Part by mass |
| Mirin | 200 | " |
| Sugar | 100 | " |
| Yeast extract | 6 | " |
| Water | 194 | " |
| Total | 1000 | |

Well-trained 5 panelists tasted the mentsuyu not added with the katsuobushi-like emulsified flavor composition and the katsuobushi-like compounded flavor composition-added mentsuyu for organoleptic evaluation. As a result, all the five panelists concluded that the mentsuyu added with the katsuobushi-like emulsified flavor composition of the present invention was good as given a katsuobushi-like flavor, additionally saying that the taste thereof covered enhanced umami, saltiness and sweetness, that is, the mentsuyu was extremely delicious and good.

Example 211: Katsuobushi-Like Powdery Flavor Composition

As an aqueous phase, 70 g of gum arabic and 20 g of trehalose were dissolved in 150 g of water, and sterilized by heating at 85 to 90° C. for 15 minutes, and then cooled down to 40° C. As an oily phase, 10 g of the reference product 203 was added thereto and mixed, and then emulsified with a TK-homogenizer to produce an O/W emulsified composition. The emulsified composition was spray-dried, using a mobile minor spray drier by Niro, at an inlet temperature of 140° C. and an outlet temperature of 75° C. to produce 95 g of a katsuobushi-like powdery flavor composition (invention product 203: 2-(3-benzyloxypropyl)pyridine concentration 0.1% by mass).

Example 212: Addition of Katsuobushi-Like Powdery Flavor Composition to Powdery Ramen Soup Powdery ramen soup was prepared according to the formulation of Table 26. 1% by mass of the invention product 203 was further added thereto.

TABLE 26

| | Amount Added (part by mass) |
|---|---|
| Edible salt | 360 |
| Powdered soy sauce | 220 |
| Sodium L-glutamate | 120 |
| Meat extract powder | 100 |
| Sugar | 80 |
| Seafood extract powder | 30 |
| Vegetable extract powder | 20 |
| Spice powder | 10 |
| Sodium succinate | 5 |
| Dextrin | 55 |
| Total | 1000 |

Powdery ramen soup added with the invention product 203 and that not added with it were prepared each in an amount of 10 g, 600 ml/one of hot water (70° C.) was added to dilute them, and well-trained 5 panelists tasted them for organoleptic evaluation. As a result, all the five panelists concluded that the ramen soup added with the katsuobushi-like powdery flavor composition of the invention was better as given a katsuobushi-like flavor, additionally saying that the composition-added ramen soup was an extremely better-tasting one as given greatly enhanced umami, saltiness and sweetness.

Example 213: Milk-Like Emulsified Flavor Composition

According to the formulation of the following Table 27, milk-like compounded flavor compositions (reference product 204 and reference product 205) were prepared.

TABLE 2

Milk-like Compounded Flavor Formulation

| | Reference Product 204 | Reference Product 205 | |
|---|---|---|---|
| Vanillin | 25.0 | 25.0 | part by mass |
| Ethylvanillin | 35.0 | 35.0 | " |
| Maple lactone | 2.5 | 2.5 | " |
| Ethylmaltol | 3.5 | 3.5 | " |
| γ-undecalactone | 2.0 | 2.0 | " |
| γ-nonalactone | 10.0 | 10.0 | " |
| δ-decalactone | 2.5 | 2.5 | " |
| Acetylmethylcarbinol | 3.0 | 3.0 | " |
| Diacetyl | 7.0 | 7.0 | " |
| Butyric acid | 5.0 | 5.0 | " |
| 2-(3-benzyloxypropyl)pyridine | 10.0 | — | " |
| Middle chain fatty acid triglyceride | balance | balance | " |
| Total | 1000.0 | 1000.0 | " |

100 g of the milk-like compounded flavor composition of Table 27 (referenced product 204: 2-(3-benzyloxypropyl)pyridine concentration 1.0 mass %, or reference product 205: not using 2-(3-benzyloxypropyl)pyridine) as an oily phase, and a solution of 312.5 g of glycerin, and 22.5 g of decaglycerinmonopalmitake dissolved in 65 g of ion-exchanged water as an aqueous phase were prepared. The two were mixed by stirring with a TK-homogenizer (manufactured by Primix Corporation) at 8000 rpm for 10 minutes for emulsification. Thus, a milk-like emulsified flavor composition in the form of an O/W emulsion was prepared, whose absorbance at a wavelength 680 nm in 1/2000 dilution with ion-exchanged water was 0.2 Abs (invention product 204: 2-(3-benzyloxypropyl)pyridine concentration 0.2% by mass, comparative product 202: not using 2-(3-benzyloxypropyl)pyridine).

Example 214: Addition of Milk-Like Emulsified Flavor Composition to Lacto-Ice

According to the formulation of the following Table 28, lacto-ice was prepared, and 0.01% of the milk-like compounded flavor composition of the invention product 204 or the comparative product 202 was added thereto (2-(3-benzyloxypropyl)pyridine concentration in the lacto-ice using the invention product 204, 0.2 ppm). For preparing lacto-ice, all the materials were dissolved by heating and emulsified with a homogenizer at 150 kg/cm², and then aged overnight at 10° C. This was frozen with a freezer, and then hardened up at −40° C. for 1 hour to give lacto-ice.

TABLE 28

| Sweetened condensed milk | 4 | part by mass |
|---|---|---|
| Skim milk | 7 | " |
| Vegetable oil and fat | 9 | " |
| Sugar | 10 | " |
| Egg yolk | 12.5 | " |
| Stabilizer | 0.3 | " |
| Emulsifier | 0.4 | " |
| Vanilla flavor | 0.1 | " |
| water | balance | " |
| Total | 100 | " |

Well-trained 5 panelists tasted the lacto-ice added with the milk-like emulsified flavor composition of the comparative product 202 or the invention product 204, and the non-added lacto-ice for organoleptic evaluation. As a result, all the five panelists first concluded that the lacto-ice added with the comparative product 202 provided better milk-like flavor than the lacto-ice not added with the flavor. Further, all the five panelists concluded that the lacto-ice added with the invention product 204 provided better milk-like flavor than the lacto-ice added with the comparative product 202 and that, regarding taste, the former provided enhanced umami, sweetness and milk richness and was extremely delicious and good.

Example 215: Milk-Like Powdery Flavor Composition

As an aqueous phase, 70 g of gum arabic and 20 g of trehalose were dissolved in 150 g of water, and sterilized by heating at 85 to 90° C. for 15 minutes, and then cooled down to 40° C. As an oily phase, 10 g of the reference product 204 was added thereto and mixed, and then emulsified with a TK-homogenizer to produce an O/W emulsified composition. The emulsified composition was spray-dried, using a mobile minor spray drier by Niro, at an inlet temperature of 140° C. and an outlet temperature of 75° C. to produce 95 g of a milk-like powdery flavor composition (invention product 205: 2-(3-benzyloxypropyl)pyridine concentration 0.1% by mass).

Example 216: Addition to Aqueous Solution of Skim Milk

Skim milk, and a mixture of 99 parts by mass of skim milk and 1 part by mass of the invention product 205 were prepared by thorough mixing. 10 parts by mass of each was mixed with 90 parts by mass of water to prepare a mixture solution (aqueous solution of skim milk). Well-trained 5 panelists tasted these for organoleptic evaluation. As a result, all the five panelists concluded that the aqueous solution of skim milk added with the invention product 205 was better than the non-added aqueous solution of skim milk in that the former provided stronger milky flavor, stronger umami and sweetness, and stronger milk richness, namely, the former had an extremely good milky taste.

Example 217: Pineapple-Like Emulsified Flavor Composition

According to the formulation of the following Table 29, a pineapple-like compounded flavor composition was prepared (reference product 206).

TABLE 29

| Ethyl acetate | 12 | part by mass |
|---|---|---|
| Ethyl butyrate | 10 | " |
| Isoamyl acetate | 4 | " |
| Isoamyl valerate | 2.2 | " |
| Isobutyric acid | 2.8 | " |
| Isovaleric acid | 1.2 | " |
| Allyl caproate | 1.4 | " |
| Ethyl caproate | 0.8 | " |
| Ethyl caprylate | 0.6 | " |
| Ethyl caprate | 0.8 | " |
| Isoamyl alcohol | 1.4 | " |
| Diethyl malonate | 1.2 | " |
| Citral | 0.6 | " |
| Linalool | 0.2 | " |
| Maltol | 0.8 | " |
| 2-(3-benzyloxypropyl)pyridine | 0.2 | " |
| Middle-chain fatty acid triglyceride | balance | " |
| Total | 1000 | |

As an oily phase, 100 g of the pineapple-like compounded flavor composition of Table 29 (reference product 206: 2-(3-(benzyloxypropyl)pyridine concentration 0.02% by mass), and as an aqueous phase, 312.5 g of glycerin and 22.5 g of decaglycerin monooleate dissolved in 65 g of ion-exchanged water were prepared, and the two liquids were mixed by stirring with a TK-homogenizer (manufactured by Primix Corporation) at 8000 rpm for 10 minutes for emulsification. Thus, a pineapple-like emulsified flavor composition in the form of an O/W emulsion was prepared, whose absorbance at a wavelength 680 nm in 1/2000 dilution with ion-exchanged water was 0.2 Abs (invention product 206: 2-(3-benzyloxypropyl)pyridine concentration 40 ppm).

Example 218: Addition of Pineapple-Like Compounded Flavor Composition to Sherbet According to the formulation of the following Table 30, sherbet was prepared, and 0.2% of the pineapple-like emulsified flavor composition of the invention product 206 was added thereto (2-(3-benzyloxypropyl)pyridine concentration 80 ppb).

Five panelists ate these sherbet products for organoleptic evaluation. As a result, all the five panelists concluded that the sherbet added with the invention product 206 had fresher and better pineapple characteristics of natural impression than the non-added sherbet, saying that, regarding the taste thereof, the former realized better umami and sweetness than the latter.

TABLE 30

| Sugar | 10 | part by mass |
|---|---|---|
| Starch syrup (75%) | 6 | " |
| Fructose sucrose liquid sugar (75%) | 5 | " |
| Citric acid (crystal) | 0.1 | " |
| 20% pineapple juice | 10 | " |
| Water | balance | " |
| Total | 100 | " |

While the present invention has been described in detail and with reference to specific embodiments thereof, it will be apparent to one skilled in the art that various changes and modifications can be made therein without departing from the spirit and scope thereof.

The present disclosure relates to the subject matter contained in International Application No. PCT/JP2016/061077, filed Apr. 5, 2016, Japanese Patent Application No. 2015-083656 filed on Apr. 15, 2015, Japanese Patent Application No. 2015-181420 filed on Sep. 15, 2015 and Japanese Patent Application No. 2015-206337 filed on Oct. 20, 2015, the contents of which are expressly incorporated herein by reference in their entirety. All the publications referred to in the present specification are also expressly incorporated herein by reference in their entirety.

The foregoing description of preferred embodiments of the invention has been presented for purposes of illustration and description, and is not intended to be exhaustive or to limit the invention to the precise form disclosed. The description was selected to best explain the principles of the invention and their practical application to enable others skilled in the art to best utilize the invention in various embodiments and various modifications as are suited to the particular use contemplated. It is intended that the scope of the invention not be limited by the specification, but be defined claims.

The invention claimed is:

1. A compound represented by the following formula (4) or a salt thereof:

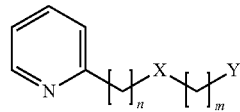

(4)

wherein, in formula (4), n=2, 3, 4 or 5, m=1 or 2, provided that a case where n=2 and m=1 is excluded, X represents O or S, and Y represents the following formula (5) or (6):

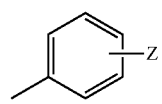

(5)

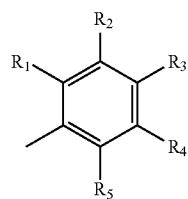

(6)

wherein, in the above formula (5), Z represents a hydrogen atom, an alkyl group having 1 to 4 carbon atoms or a group OR, where R represents a hydrogen atom or an alkyl group having 1 to 4 carbon atoms, provided that a case where n=3 or 4 and m=1, X is O and Z is H or a methyl group is excluded, wherein, in the above formula (6), $R_1$ to $R_5$ each represent a hydrogen atom or a methyl group, and at least two of $R_1$ to $R_5$ are methyl groups.

2. The compound according to claim 1, wherein Y represents formula (5) and Z represents a hydrogen atom or a group OR, where R represents a hydrogen atom or an alkyl group having 1 to 4 carbon atoms.

3. The compound according to claim 1, wherein Y represents formula (5) and Z represents a hydrogen atom.

* * * * *